US012797207B2

(12) United States Patent
Orozco Castillo

(10) Patent No.: US 12,797,207 B2
(45) Date of Patent: *Nov. 17, 2026

(54) SYSTEMS AND METHODS FOR PERCUTANEOUS SPINAL INTERBODY FUSION (PSIF)

(71) Applicant: MIS Spine IP, LLC, Rowlett, TX (US)

(72) Inventor: Ludwig David Orozco Castillo, Parker, TX (US)

(73) Assignee: MIS Spine IP, LLC, Rowlett, TX (US)

( * ) Notice: Subject to any disclaimer, the term of this patent is extended or adjusted under 35 U.S.C. 154(b) by 140 days.

This patent is subject to a terminal disclaimer.

(21) Appl. No.: 18/961,611

(22) Filed: Nov. 27, 2024

(65) Prior Publication Data

US 2026/0144533 A1 May 28, 2026

Related U.S. Application Data

(63) Continuation of application No. 17/583,281, filed on Jan. 25, 2022, now Pat. No. 12,178,720, which is a (Continued)

(51) Int. Cl.
*A61F 2/46* (2006.01)
*A61B 17/02* (2006.01)
(Continued)

(52) U.S. Cl.
CPC ........ *A61F 2/4611* (2013.01); *A61B 17/0206* (2013.01); *A61B 17/686* (2013.01); (Continued)

(58) Field of Classification Search
CPC ..... A61B 17/16; A61B 17/1671; A61B 17/02; A61B 17/0206; A61B 17/17; (Continued)

(56) References Cited

U.S. PATENT DOCUMENTS 5,964,761 A 10/1999 Kambin
5,976,105 A 11/1999 Marcove et al.
(Continued)

FOREIGN PATENT DOCUMENTS

CN 204219006 3/2015
CN 204233246 4/2015
(Continued)

OTHER PUBLICATIONS

Khoo, Palmer, Laich, Fessler, "Minimally Invasive Percutaneous Posterior Lumbar Interbody Fusion," Neurosurgery—Online, Nov. 2002, vol. 51, Supplement 2, Chapter 21.
(Continued)

*Primary Examiner* — Christopher J Beccia
(74) *Attorney, Agent, or Firm* — RegitzMauck PLLC; Dustin Mauck; Mike Regitz

(57) ABSTRACT

The present invention includes a novel procedure and corresponding medical devices for a Purcutaneous Spinal Interbody Fusion (PSIF). In PSIF, the surgeon performs the entire operation percutaneously without the use of a microscope, endoscope, or magnifying loupes. An adjustable retractor system is disclosed that enables the surgeon to percutaneously perform the surgery through accessing the facet joint (and later disc space) that was created by said retractor system. This retractor system provides the surgeon a safe area to work and operate without fear of damaging nerves, blood vessels, or other tissue. An expanding trial may be inserted into and removed from the disc space through the interior of the retractor system to determine the proper size for the expandable cage. The retractor system also enables the expandable cage to be inserted into the disc space.

20 Claims, 21 Drawing Sheets

Related U.S. Application Data continuation of application No. 16/455,894, filed on Jun. 28, 2019, now Pat. No. 11,259,940.

(51) Int. Cl.

| | |
|---|---|
| ***A61B 17/68*** | (2006.01) |
| ***A61B 17/70*** | (2006.01) |
| ***A61F 2/44*** | (2006.01) |
| ***A61M 29/00*** | (2006.01) |
| *A61B 17/16* | (2006.01) |
| *A61B 17/88* | (2006.01) |

(52) U.S. Cl.

CPC ........ *A61B 17/7064* (2013.01); *A61F 2/4455* (2013.01); *A61M 29/00* (2013.01); *A61B 17/1615* (2013.01); *A61B 17/1671* (2013.01); *A61B 17/8897* (2013.01)

(58) Field of Classification Search

CPC . A61B 17/1757; A61B 17/70; A61B 17/7064; A61B 17/7086; A61B 17/686; A61F 2/44; A61F 2/4455; A61F 2/447; A61F 2/46; A61F 2/4684; A61F 2/4611

See application file for complete search history.

(56) References Cited

U.S. PATENT DOCUMENTS

| | | | | |
|---|---|---|---|---|
| 8,353,912 | B2 | 1/2013 | Darian et al. | |
| 8,613,746 | B2 | 12/2013 | Spratt et al. | |
| 8,709,087 | B2 | 4/2014 | Cragg | |
| 9,232,953 | B2 | 1/2016 | Bono et al. | |
| 9,289,227 | B2 | 3/2016 | Lauchner | |
| 9,408,624 | B2 | 8/2016 | Molinari et al. | |
| 9,408,716 | B1 | 8/2016 | Reitblat et al. | |
| 9,504,483 | B2 | 11/2016 | Houser et al. | |
| 9,510,875 | B2 | 12/2016 | Reitblat et al. | |
| RE46,432 | E | 6/2017 | Kingsley et al. | |
| 10,105,232 | B2 | 10/2018 | Roche et al. | |
| 10,758,286 | B2 * | 9/2020 | Ammerman ....... | A61B 17/3417 |
| 11,259,940 | B2 * | 3/2022 | Orozco Castillo .......................... | A61B 17/1671 |
| 2004/0039384 | A1 | 2/2004 | Boehm et al. | |
| 2006/0206118 | A1 | 9/2006 | Kim et al. | |
| 2010/0256682 | A1 | 10/2010 | Fallin et al. | |
| 2010/0286486 | A1 * | 11/2010 | Parker ................ | A61B 17/1757 600/235 |
| 2013/0253591 | A1 | 9/2013 | Kornel | |
| 2014/0277145 | A1 | 9/2014 | Reitblat et al. | |
| 2014/0277499 | A1 | 9/2014 | Ainsworth et al. | |
| 2015/0230834 | A1 * | 8/2015 | Cannestra .......... | A61B 17/1757 606/279 |
| 2015/0374354 | A1 * | 12/2015 | Boyd ................. | A61B 17/1757 600/204 |
| 2016/0157885 | A1 | 6/2016 | Lauchner | |
| 2017/0209158 | A1 | 7/2017 | Williams | |

FOREIGN PATENT DOCUMENTS

| | | |
|---|---|---|
| CN | 104905850 | 4/2017 |
| KR | 20060094733 | 8/2006 |
| WO | WO2007120903 | 10/2007 |

OTHER PUBLICATIONS

Xiao, Xiong, Zhang, Jian, Zheng, Luo, Dai, Zhang, "Percutaneous Posterior-Lateral Lumber Interbody Fusion for Degenerative Disc Disease Using a B-Twin Expandable Spinal Spacer," Springer, Sep. 26, 2009.

* cited by examiner

SYSTEMS AND METHODS FOR PERCUTANEOUS SPINAL INTERBODY FUSION (PSIF)

PRIORITY CLAIM

This application claims priority to and is a continuation application of U.S. patent application Ser. No. 17/583,281 that was filed on Jan. 25, 2022, which claims priority to and is a continuation of U.S. Pat. No. 11,259,940 (patent app. Ser. No. 16/455,894) that was filed on Jun. 28, 2019. These applications are hereby incorporated by reference.

TECHNICAL FIELD

The present invention relates generally to systems and apparatuses that assist with Percutaneous Spinal Interbody Fusion (PSIF) or Percutaneous Posterior Lumbar Interbody Fusion (PePLIF), and more specifically, to the systems and methods for fusing two or more vertebrae together and inserting a disc implant to assist with any degenerative issues or injuries to a lumbar disc.

BACKGROUND OF THE INVENTION

Back and spinal problems affect countless patients in the United States and throughout the world and spinal fusion is one procedure that is designed to correct or improve some of these back or spinal problems. Spinal fusion is a procedure that permanently connects two or more vertebrae in your spine to improve stability, correct a deformity, or reduce pain. Spinal surgeons may recommend fusion to (1) correct spinal deformities, such as scoliosis, (2) stabilize the spine if there is excessive motion between two vertebrae, which can be caused by arthritis, or (3) stabilize the spine after removal of a damaged or herniated disk. Due to pain, comfort, and mobility issues that accompany these back or spinal problems, successful spinal fusion surgery can greatly improve the quality of life for a patient. However, any surgery affecting or surrounding the spine becomes very serious due to risks of damaging the spinal cord and the nerves that connect to the spinal cord. One wrong move or improper cut may lead to grave consequences for the rest of the patient's life.

Thus, doctors and medical device companies continue to advance the treatment and surgical procedures offered for spinal fusion in the lumbar region of the spine. The spine and corresponding vertebrae were designed to protect the spinal cord and connected nerves, so it can be difficult to access the desired area for this procedure. Different procedures that involve different tools, systems, devices, and methods have been developed and there are numerous considerations to weigh when choosing a procedure. For example, does the surgeon want to access the desired vertebrae from the anterior or posterior of the patient? How large should the incisions be for the surgery? Since the disc space between two vertebrae can be difficult to view or access, how will the surgeon view the surgical area? Is a microscope or an endoscope required? How can the recovery time for the patient be improved? With these considerations in mind, a number of different procedures have been developed. And different devices and apparatuses accompany each different method.

Interbody implantation has become common with spinal fusion, so most of the conventional methods now focus on the insertion of an implant in conjunction with the fusion of the vertebrae. This disc implant is designed to replace the spinal disc and provide anterior support for the vertebrae that becomes fused together. One method of lumbar interbody fusion is the Anterior Lumbar Interbody Fusion (ALIF). This method accesses the disc space through the anterior of the patient or through the abdominal area. Since the disc space is located at the anterior portion of the vertebrae, the surgeon may be able to view the desired area more easily because the vertebrae are not blocking the view of the disc space. However, the surgeon must move numerous organs, veins, arteries, and nerves out of the way to get to the disc space at the spine. Anterior access to the spine can pose numerous potential risks of collateral damage to organs, veins, or arteries, leads to larger incisions in the abdominal area, and can slow the recovery of the patient.

Another method is Direct Lateral Lumbar Interbody Fusion (DLIF). This method accesses the disc space laterally through the patient's side. Due to the location of the vertebrae, the surgeon may have a difficult time viewing the desired area due to shape of the vertebrae and the distance to the disc space. This procedure often involves use of a microscope of endoscope due to the lack of viewing area for the disc space. The surgeon must also move or avoid organs, veins, arteries, and nerves to get to the disc space. Lateral access to the spine poses similar risks of collateral damage, can slow recovery of the patient, and can lead to less than optimal results.

The Posterior Lumbar Interbody Fusion (PLIF) method accesses the disc space through the posterior of the patient. The surgeon cannot see the disc space through the vertebrae because the bone matter that is designed to protect the spinal cord. Conventional methods require a microscope or an endoscope to assist with the surgeon's view of the desired area. The lack of vision may lead to lengthy surgeries, less than optimal results, and risks of lacerating a nerve, sac of nerves, or dural elements. In some PLIF surgeries, large amounts of bone from the vertebrae must be removed to improve vision and access.

Oblique Lateral Interbody Fusion (OLIF) was developed as a cross between the ALIF and the DLIF. This method accesses the disc space from the front and the side of the body (passing in a trajectory about halfway between the middle of the stomach and the side of the body). However, many of the drawbacks mentioned above with respect to the ALIF and DLIF remain.

A procedure called Transforaminal Interbody Lumbar Fusion (TLIF) has also been developed to access the disc space through the foramina, which are openings through which the nerve roots exit the spine. The surgeon is required to remove the lamina and the facet joint (bone matter) during the procedure and it is crucial to protect the nerves traveling through the foramina. This procedure can be risky due to the proximity to the nerves of the patient and the amount of bone that must be removed to gain access to the disc space.

Due to the manner of accessing the disc space and the circumstances surrounding each procedure, different devices, apparatuses, systems, and methods have been developed to accomplish each type of spinal fusion. However, each method has its drawbacks and problems, including longer recovery times, less than optimal interbody fusion, large incisions, lack of access to the disc space, and other concerns. Patients with back and spinal problems need a new solution that addresses these drawbacks and improves the outcome for the patient.

BRIEF SUMMARY OF THE INVENTION

The present invention includes a novel procedure and corresponding medical devices for a Percutaneous Spinal Interbody Fusion (PSIF) or a Percutaneous Posterior Lumbar Interbody Fusion (PePLIF). In PePLIF, the surgeon performs the entire operation percutaneously without the use of a microscope, endoscope, or magnifying loupes. Indirect visualization may be obtained with a wide range of navigation options such as C-arm fluoroscopy or more advance CT/MRI based systems. This procedure offers major advantages, including reduced surgical time, single prone patient positioning, reduced tissue manipulation/disruption, solid bilateral interbody support, anatomical reconstitution and fusion, avoidance of abdominal, lateral, and oblique access (and related side effects and morbidity), simplicity of procedure for surgeons familiar with percutaneous spinal procedures, and cost savings when compared to other procedures. These advantages lead to less blood loss, less post-operative pain, shortened hospital stays, reduced recovery times, improved recovery and spinal stability, overall cost savings, and flexible use in inpatient and outpatient settings.

One of the key advantages of the present invention is the ability of the surgeon to access the surgery percutaneously. One or more dilator/retractor systems may be used in conjunction with a pedicle tower to provide this access area. The surgeon may view the working area through X-rays, C-arm fluoroscopy, or a navigation system. After the pedicle screw and its pedicle tower are inserted in the patient, a first soft tissue dilator may be used to gently move soft tissue, skin, fascia, and muscle out of the way. Then dilators increasing in size may be slid into place outside of the first soft tissue dilator to increase the size of the safe area. Finally, a soft tissue retractor is slid and locked into place on the outside of the other dilators to provide the soft tissue retractor safe space. Later in the procedure a first disc dilator may be used to protect the surgeon from the nerves, sac of nerves, dural elements, and arteries. Then dilators increasing in size may be slid into place outside of the first disc dilator to increase the size of the safe area. Finally, a disc retractor is slid and locked into place on the outside of the other dilators to provide the disc retractor safe space. In these safe spaces, the surgeon can percutaneously access the area that needs to be worked on and dilate and retract the soft tissues, skin, fascia, and muscle with the soft tissue system and dilate and retract the nerves, sac of nerves, dural elements, and arteries with the disc system.

An advantage of the retractor system is that it is adjustable for all patient sizes. A tall patient may have a further distance between the inferior pedicle and the disc space, while a shorter patient may not. This may be considered the height of the first soft tissue dilator and the pedicle screw/tower. Diameter size of the dilator and retractor system may also be an issue with different size patients. If the patient has a tall or large disc, a larger last disc dilator or retractor may be used. Additionally, different patients may have different shapes and contours of the spine which could lead to different angles required to access the disc space. A surgeon may adjust the retractor space accordingly. An adjustment of the angle of the retractor system can be made by twisting or turning the pedicle tower and locking it into place. The length of the retractor space may also be adjusted by using different size dilators. For example, if a longer retractor space is required, then a longer first dilator may be used to stretch the retractor safe space. The remaining dilators and retractor would then stretch out in response to the length of the first dilator. Or the surgeon may be able to select a longer first dilator and a longer retractor to handle a patient that requires a longer retractor space.

Another key advantage of the present invention is an expandable disc trial that may be inserted, expanded, and removed by the surgeon through the disc retractor safe space. An expandable disc trial device that holds the expandable trial may be held and controlled by the surgeon. The device may be hollow to provide air or fluid to fill the expandable trial when it is inserted in the disc space. After the disc space has been prepared or suctioned, the expandable trial is inserted in the disc space and air, water, or other material can flow into the expandable trial for expansion. An endless screw and/or expandable jack may be used as a mechanical expandable trial. Once the expandable trial is at the proper size, the surgeon may remove the expandable trial to determine the proper size for the implant or cage. The device may be able to track how much air or water has been pumped into the expandable trial or the distance of expansion of the mechanical trial to assist in determining the proper size of the cage or implant. The expandable trial may also be controlled and expanded by the surgeon through mechanical or electrical means. In some embodiments, the expandable trial may be inserted with a low profile and then actuated to expand once it is inserted in the proper area.

An expandable cage that may be used in the retractor safe space is further disclosed. The expandable cage may include a screw mechanism that is used by the surgeon to expand the cage. Through this screw mechanism, an upper plate of the expandable cage may extend or contract based upon the movement of the screw. An x-shape lift mechanism may also be used to extend or contract the upper plate. The cage may be hollow and the plates that make up the expandable cage may have numerous holes or voids for the influx of bone material after insertion. After the cage has been expanded to the proper size by the surgeon, bone material can be pumped in through an expandable cage insertion device such that it overflows and pours out of the expandable cage.

The steps of this procedure include: (1) insert pedicle screw and tower on the inferior pedicle of the segment to be fused; (2) insert soft tissue dilators and retractor; (3) remove bone; (4) insert disc dilators and retractor; (5) remove disc; (6) disc expansion and expandable interbody device insertion; and (7) superior pedicle screw insertion with rods and set screws. These portions of the surgery can be done through the soft tissue retractor safe space and the disc retractor safe space, thus allowing the surgeon to operate percutaneously without assistance from endoscopes, microscopes, or magnifying loupes. The two dilator/retractor systems provide the surgeon a safe area to work and operate without fear of damaging soft tissues, nerves, or dural elements.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

This novel PePLIF procedure combines two emerging technologies in a revolutionary spinal surgery—(1) ultrasonic bone and spinal disc removal and (2) expandable interbody cages. With the novel medical devices and procedures described herein, the surgeon may perform the entire surgery percutaneously without the use of a microscope, endoscope, or magnifying loupes. The dilators, retractors, ultrasonic bone and disc removal devices, pedicle screw towers, and other devices disclosed herein enable the surgeon to operate on the desired area through indirect visualization with assistance from a wide range of navigation options such as C-arm fluoroscopy or more advanced CT/MRI based systems.

Figure 1:
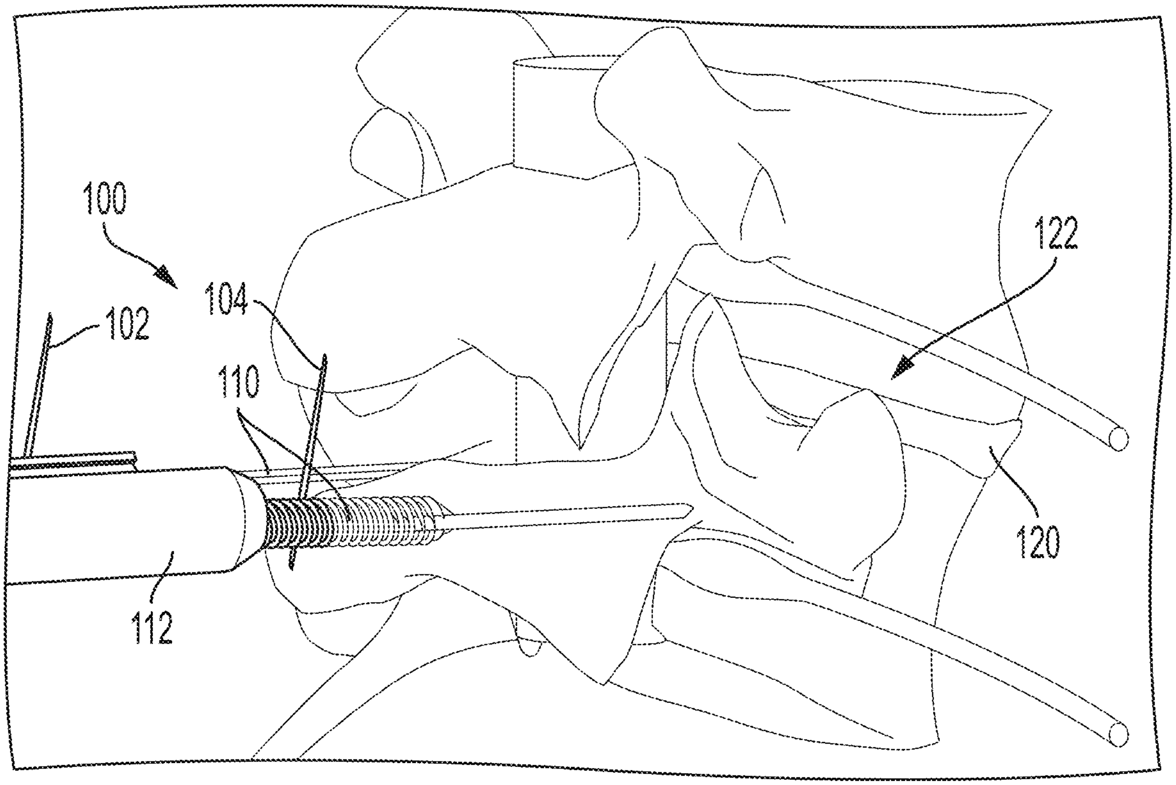
FIG. 1 shows a lateral view of a PePLIF procedure according to certain embodiments of the claimed invention.

A novel PePLIF procedure according to embodiments of the present invention begins with two paraspinal incisions (right and left) to the patient. These incisions should be made to the areas of the lumbar spine where fusion is needed. At these incision areas the surgeon places two pedicle screws (right and left) in the inferior pedicles of the interbody segment to be fused. FIG. 1 shows a side view of this portion of the PePLIF procedure where pedicle screws 110 are being inserted into the inferior pedicles of the spinal section to be fused. The right paraspinal incision 104 and the left paraspinal incision 102 are also shown on the patient. A pedicle screw tower 112 is shown in FIG. 1, which enables the surgeon to work with the pedicle screw 110, but also provides a strong support for other portions of the PePLIF procedure. There is one pedicle screw tower 112 per pedicle screw 110. After the surgeon screws in the pedicle screws 110, the pedicle screw tower 112 enters into the patient's body and draws closer to the inferior pedicles. The pedicle screw tower 112 attaches to the head of the pedicle screw 110. A vertebral disc 120 is also shown in a disc space 122. This disc space 122 can be difficult to access due to the vertebrae and other tissues protecting the spinal nerves and sac of nerves/dural sac. The surgeon must access this disc space 122, while avoiding the dural sac and attached nerves to accomplish the PePLIF procedure.

Figure 2:
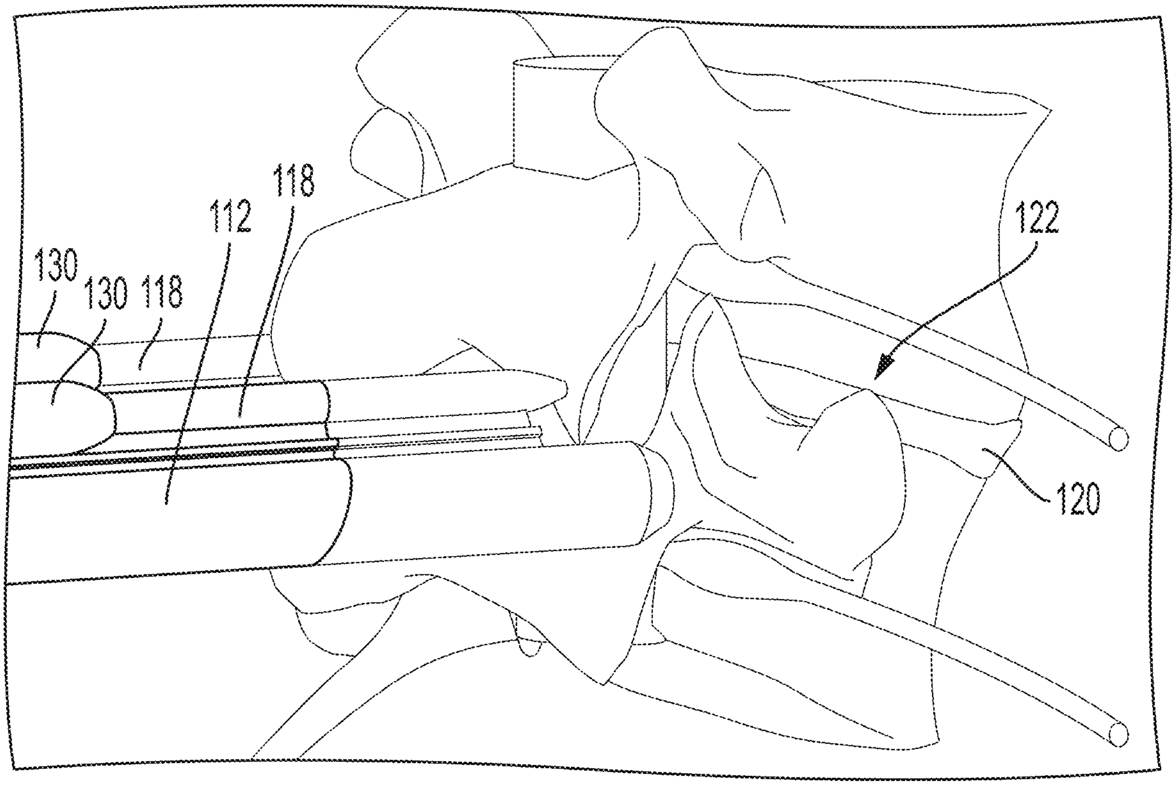
FIG. 2 shows a lateral view of a PePLIF procedure according to certain embodiments of the claimed invention.

FIG. 2 shows a side view of this portion of the PePLIF procedure where the pedicle screws 110 are fully inserted in the inferior pedicles of the interbody section. In this figure, the pedicle screw tower 112 is fully inserted adjacent to the pedicle. The pedicle screw tower 112 will be further described with reference to FIG. 15. In some embodiments, after the pedicle screws 110 and corresponding pedicle screw towers 112 are inserted into the pedicle, right and left rods may be inserted with the assistance of the pedicle screw towers 112. However, this complete pedicle screw tower is not shown if FIGS. 1 and 2 to make the remaining procedure and corresponding components easier to view and describe. This tower 112 will provide support for the dilators and retractors needed for the surgery. Typically, there is movement in all directions between the pedicle screw 110 and the pedicle screw head, which is attached to the pedicle screw tower 112. Because of this movement, the surgeon will align the long axis of the pedicle screw tower 112 with the direction of the disc space and then lock the pedicle screw tower 112 to the pedicle screw 110. This helps to align a soft tissue dilator/retractor system with the disc space 122. As shown in FIG. 2, a first soft tissue dilator 118 may be applied superior to the pedicle screw tower 112. The first soft tissue dilator 118 may be attached to the pedicle screw tower 112 through a fitting, rail, slider, or other mechanism that allows the dilator 118 to remain in the same orientation with the pedicle screw tower 112 as it moves towards the inferior pedicle. More specifically, the pedicle tower 112 moves toward the inferior pedicle, but the soft tissue dilators and retractors move toward the facet joint (which is above the inferior pedicle). This way the surgeon ensures that the dilator is going bilaterally into the correct position—the facet joints. Then a second soft tissue dilator 130 may be applied over the first soft tissue dilator 118 to increase the access area above the pedicle screw tower 112. As will discussed further herein, the soft tissue dilators 118, 130 line up with the area of the vertebrae that will need to be removed for the surgeon to access the disc space 122. The soft tissue dilators and retractor (not shown) will be further described with reference to FIG. 16.

Figure 3:
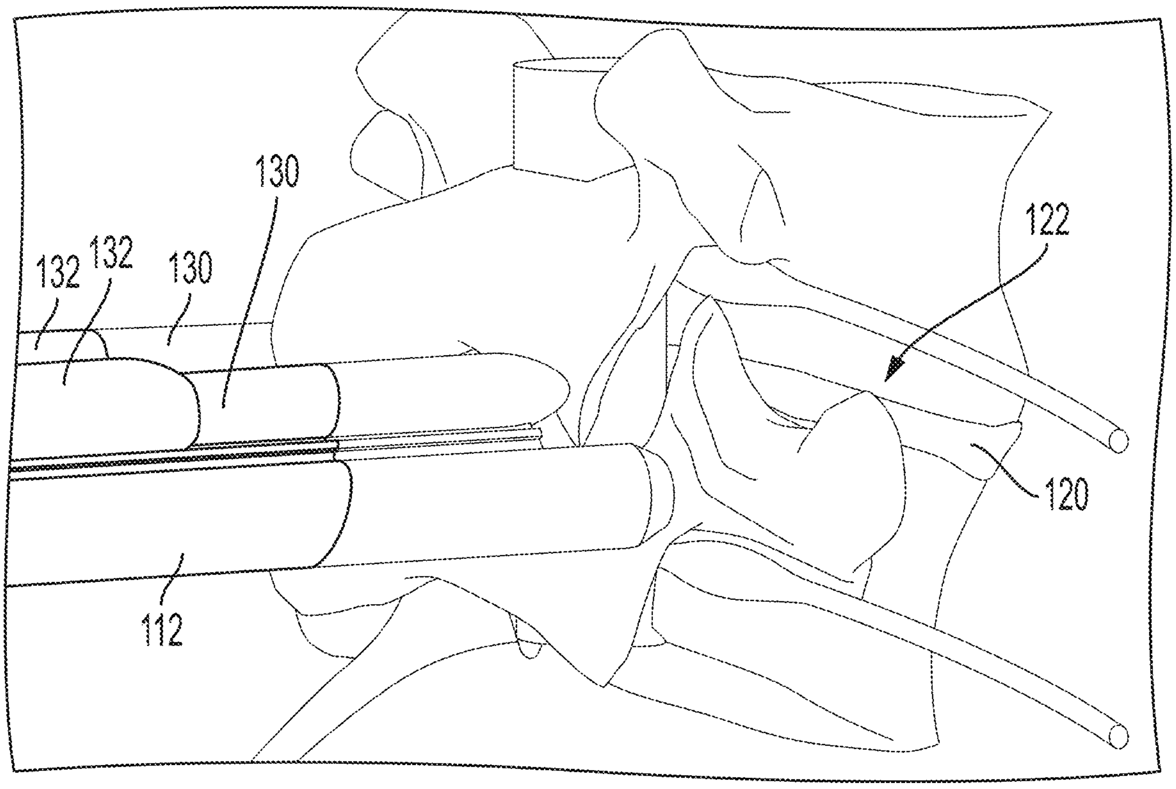
FIG. 3 shows a lateral view of a PePLIF procedure according to certain embodiments of the claimed invention.

FIG. 3 shows a side view of this portion of the PePLIF procedure where a third soft tissue dilator 132 is applied over the second dilator 130. This further increases the access area above the pedicle screw tower 112. The soft tissue dilators 118, 130, 132 are designed to provide access while gently moving any soft tissue out of the way so that the surgeon can work in the desired area without fear of cutting or damaging the skin, subcutaneous fat, fascia, or muscles. The further addition of dilators will increase the access area above the pedicle screw tower 112. In some embodiments, the inner soft tissue dilators may be removed after the outer soft tissue dilators are applied. This way only one soft tissue dilator may be connected to the initial soft tissue dilator and the pedicle screw tower 112. There may be multiple dilators in the patient at any given time.

Figure 4:
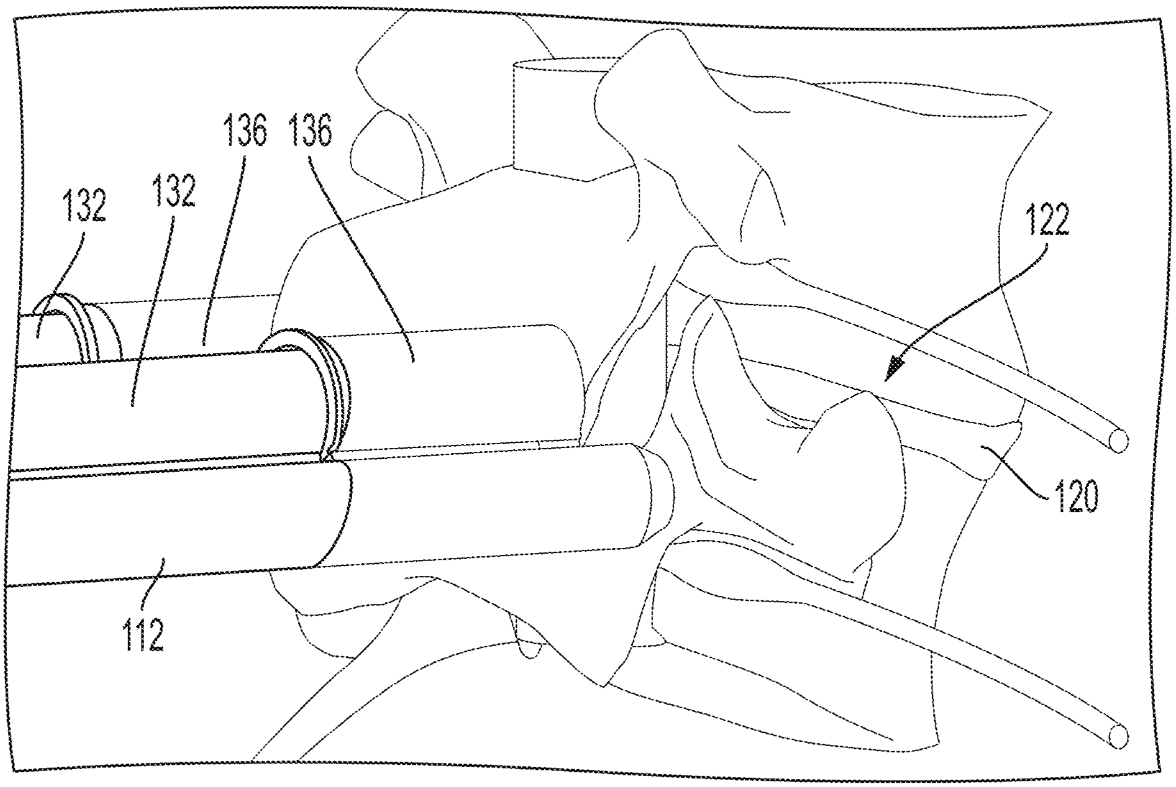
FIG. 4 shows a lateral view of a PePLIF procedure according to certain embodiments of the claimed invention.
Figure 5:
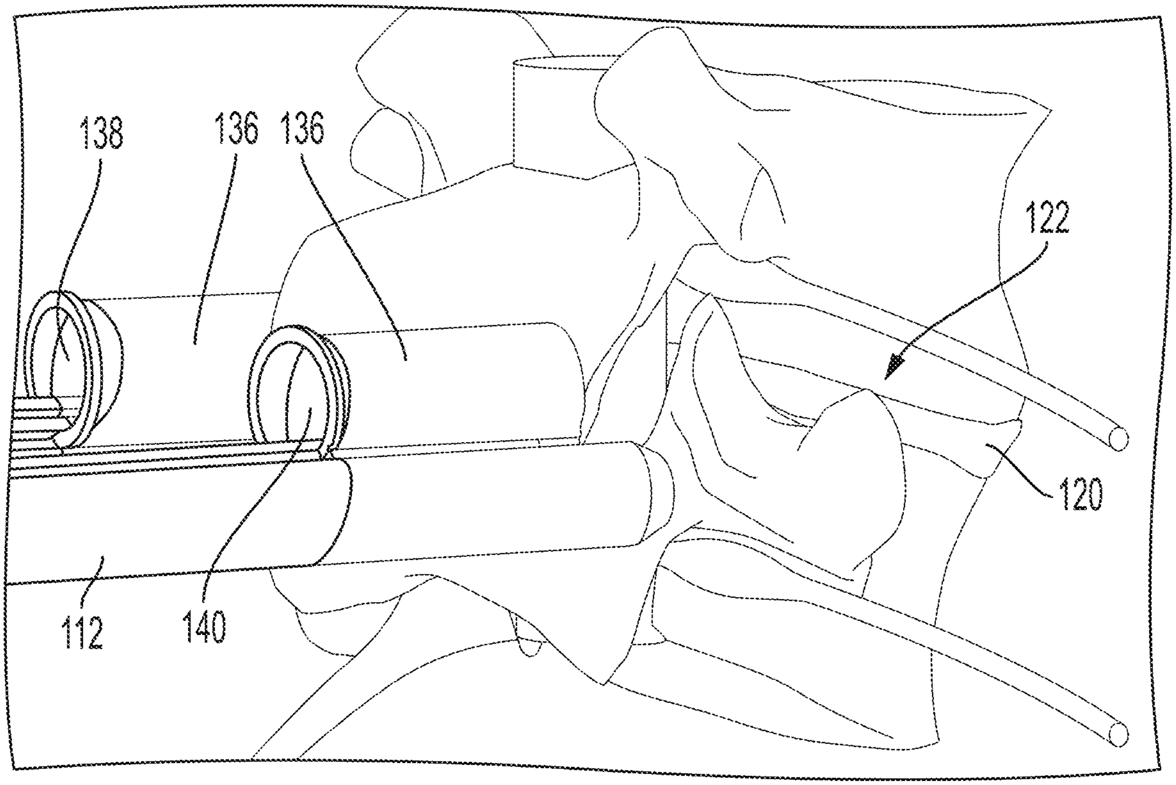
FIG. 5 shows a lateral view of a PePLIF procedure according to certain embodiments of the claimed invention.

FIG. 4 shows a side view of this portion of the PePLIF procedure where a soft tissue retractor 136 is applied over the third soft tissue dilator 132. The soft tissue retractor 136 may be attached to the pedicle screw tower 112 through a fitting, rail, slider, or other mechanism that allows the soft tissue retractor 136 to remain in the same orientation with the soft tissue dilators 118, 130, 132 and the pedicle screw tower 112. Other configurations and connections are also within the scope of the present invention (for example, in some embodiments, the soft tissue retractor 136 could be attached to the third soft tissue dilator 132). When the soft tissue retractor 136 is locked into place on the pedicle screw tower 112 it provides proper bilateral access to the facet joint. Specifically, after the soft tissue retractor 136 slides into place, the internal dilators may be removed leaving an access hole or window to the facet joint. All soft tissue dilators must be removed after the soft tissue retractor 136 is applied. In a preferred embodiment, the soft tissue retractor is only attached to the pedicle screw tower 112. FIG. 5 shows a side view of this portion of the PePLIF procedure where the soft tissue dilators (not shown) are removed and the soft tissue retractor 136 provides a right access hole or window 140 and a left access hole or window 138. At this point, the surgeon may use bone removal devices to prepare a hole in the facet joint to create a cylindrical pathway into the lower foramen.

Figure 6:
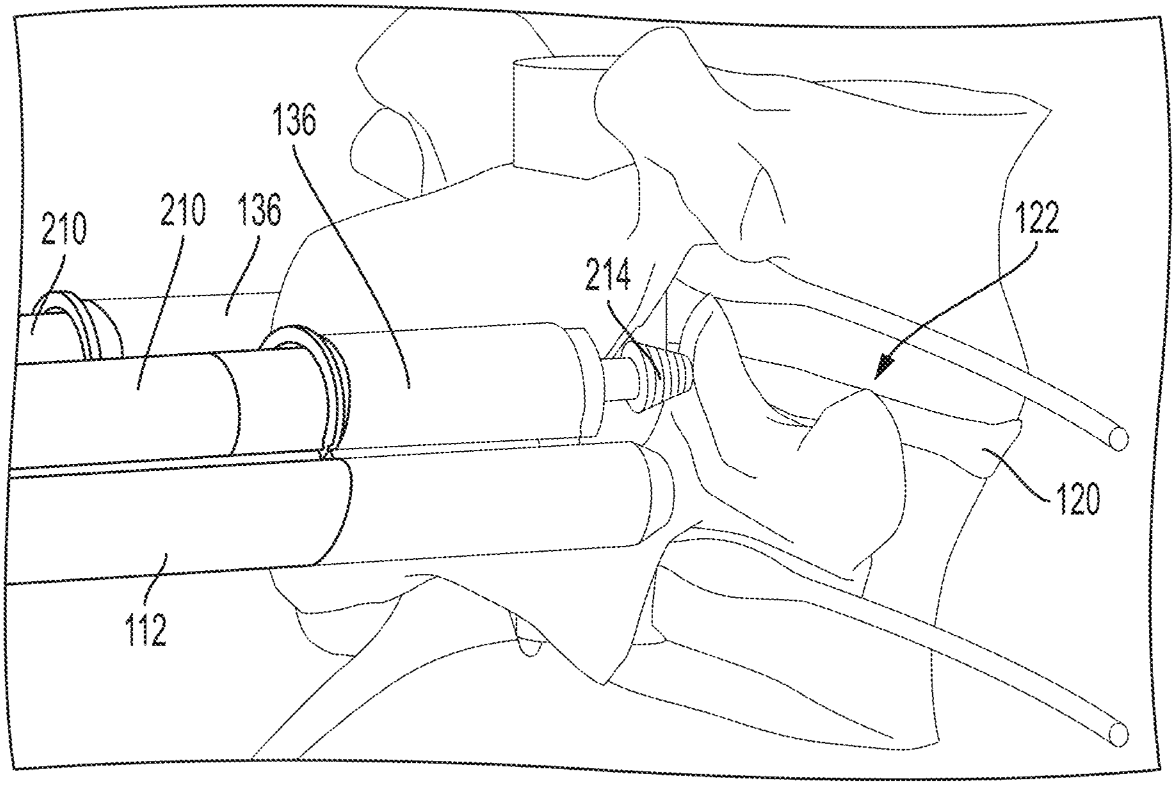
FIG. 6 shows a lateral view of a PePLIF procedure according to certain embodiments of the claimed invention.

FIG. 6 shows a side view of this portion of the PePLIF procedure where an ultrasonic bone removal and aspiration device 210 is used to create a cylindrical pathway in the facet joint. The ultrasonic bone removal and aspiration device 210 will be used on the right facet joint and the left facet joint to create two pathways into the lower foramen. An ultrasonic bur tip 214 is shown drilling into the facet joints. In some embodiments, the ultrasonic bone removal and aspiration device 210 creates an 8-12 mm cylindrical pathway into the "PeLIF work safe area" or the lateral disc space. The ultrasonic bone removal and aspiration device 210 fits in the soft tissue retractors 136 to create these pathways. Now the disc space 122 can be accessed. The ultrasonic bone removal and aspiration device 210 must also include an aspiration function that removes the displaced bone fragments from the drilling area. This can be done through an irrigation and suction component in the cylindrical tubing of the device 210. The ultrasonic bone removal and aspiration device 210 will be further described with reference to FIG. 17. A perforator drill with an aspirator or other device that can drill a hole through bone may also be used to create these cylindrical pathways in the facet joints. In some embodiments, a circular drill bit may replace the ultrasonic bur tip 214 shown in FIG. 6. In some embodiments, a portion of the ultrasonic bone removal and aspiration device fits tightly in the soft tissue retractor. Thus, when the surgeon inserts the device into the right position within the retractor, the device takes over and completes the necessary removal of bone without movement or significant intervention from the surgeon. Thus, the bone removal process becomes more automatic and the surgeon doesn't have to move the device to remove the desired material.

The "PePLIF work safe area" is on the lower foramen. The limits for the "PePLIF work safe area" include: (1) the facet joint in the posterior direction; (2) the posterior disc and the vertebral body in the anterior direction; (3) the traversing nerve root and lateral dura in the medial direction; (4) the extraforaminal area and paraspinal muscles in the lateral direction; (5) the exiting nerve root and superior pedicle in the superior direction; and (6) the inferior pedicle in the inferior direction. The dilator and retractor systems and the devices disclosed herein enable safe and protected access to this area by the surgeon.

Figure 7:
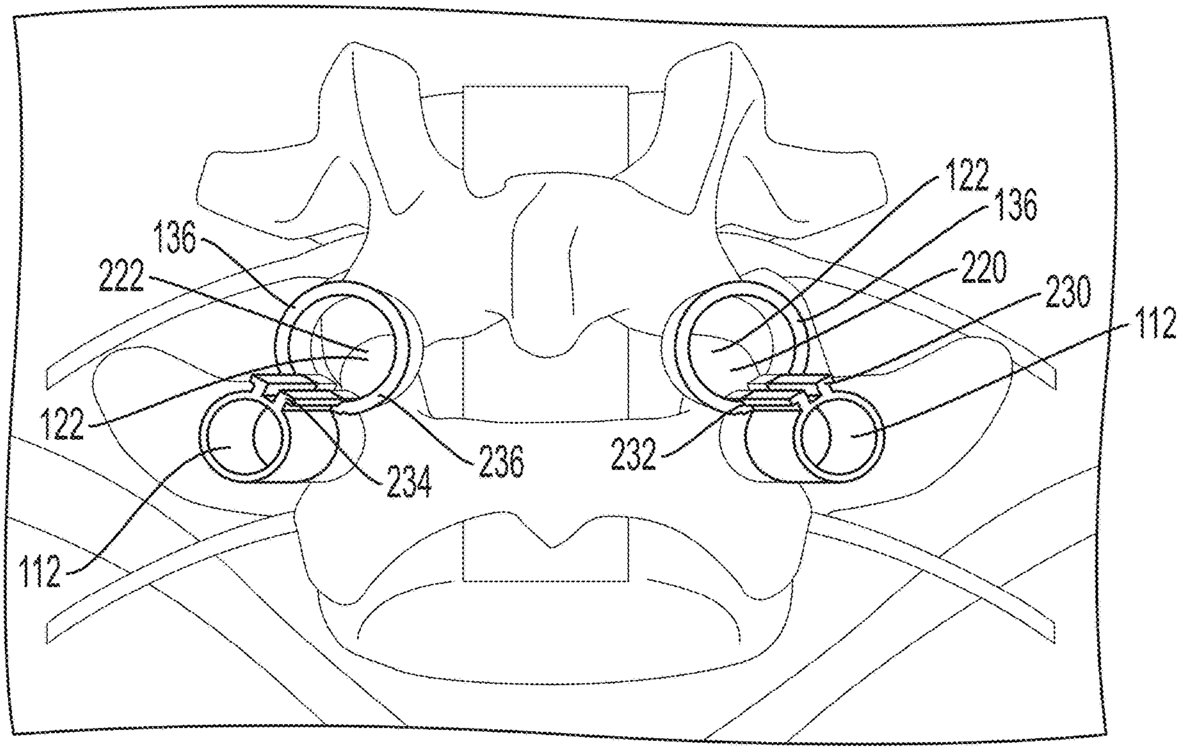
FIG. 7 shows a posterior view of a PePLIF procedure according to certain embodiments of the claimed invention.
Figure 16:
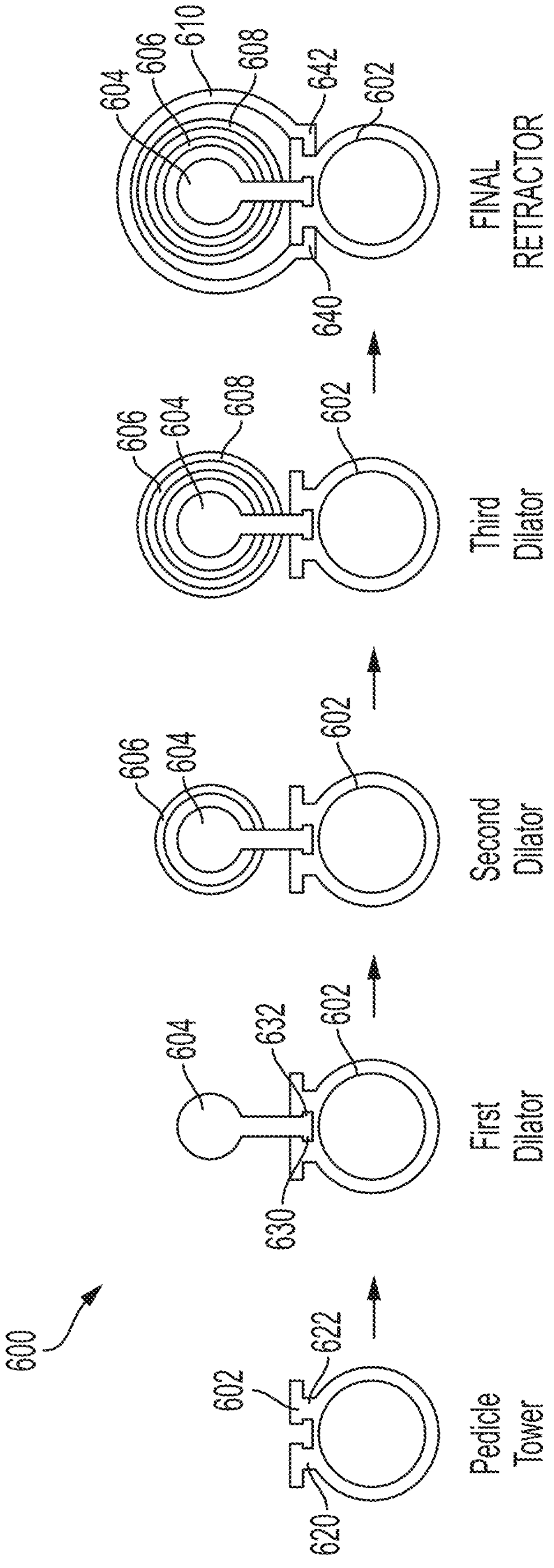
FIG. 16 shows a soft tissue dilator and retractor system that may be designed to be used in conjunction with certain embodiments of the claimed invention.

FIG. 7 shows a posterior view of this portion of the PePLIF procedure wherein the cylindrical pathway in the facet joint ("PeLIF work safe area") can be seen. This view is after the ultrasonic bone removal and aspiration device 210 has drilled the hole into the right and left facet joints and successfully aspirated the bone fragments from the drilling. The pedicle screw towers 112 remain connected to the pedicle screws that are in the vertebrae of the patient. The soft tissue retractors 136 that are connected to the pedicle screw towers 112 provided the guide for the device 210 to create the cylindrical pathways. As shown in FIG. 7, the soft tissue retractors are located superior and/or medial with respect to the pedicle screw towers 112. A set of rails or apertures 230 on the right pedicle screw tower 112 guide fingers or protrusions 232 on the right retractor 136 into the desired position. A set of rails or apertures 234 on the left pedicle screw tower 112 guide fingers or protrusions 236 on the left retractor into the desired position. The design and configuration of these rails 230, 234 and fingers 232, 236 ensure that the surgeon works in the proper location. FIG. 16 shows the soft tissue dilator and retractor system in more detail.

FIG. 7 further shows that once these cylindrical pathways are removed the surgeon has direct access to the lateral disc space 122. Direct, posterior access to the lateral disc space 122 is a great advantage of the present invention. The retractors 136 enable the surgeon to access and work within the cylindrical pathway created by the ultrasonic bone removal and aspiration device 210. However, before the surgeon can access the lateral disc space 122, the exiting nerve roots and dural elements from the spine must be safely displaced and protected with the disc dilators and disc retractor.

Figure 8:
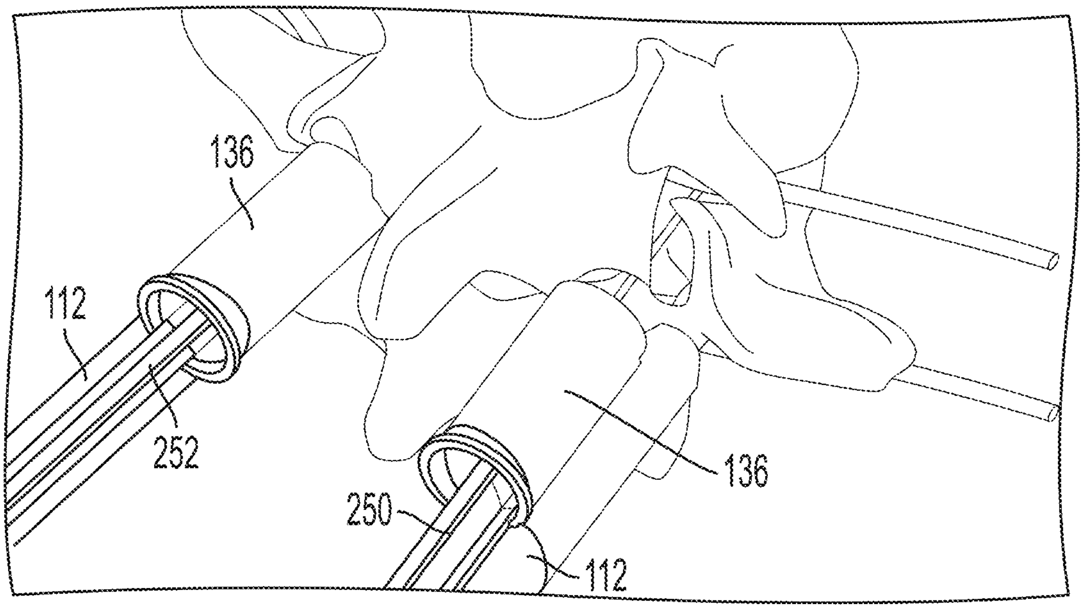
FIG. 8 shows a perspective view of a PePLIF procedure according to certain embodiments of the claimed invention.
Figure 9:
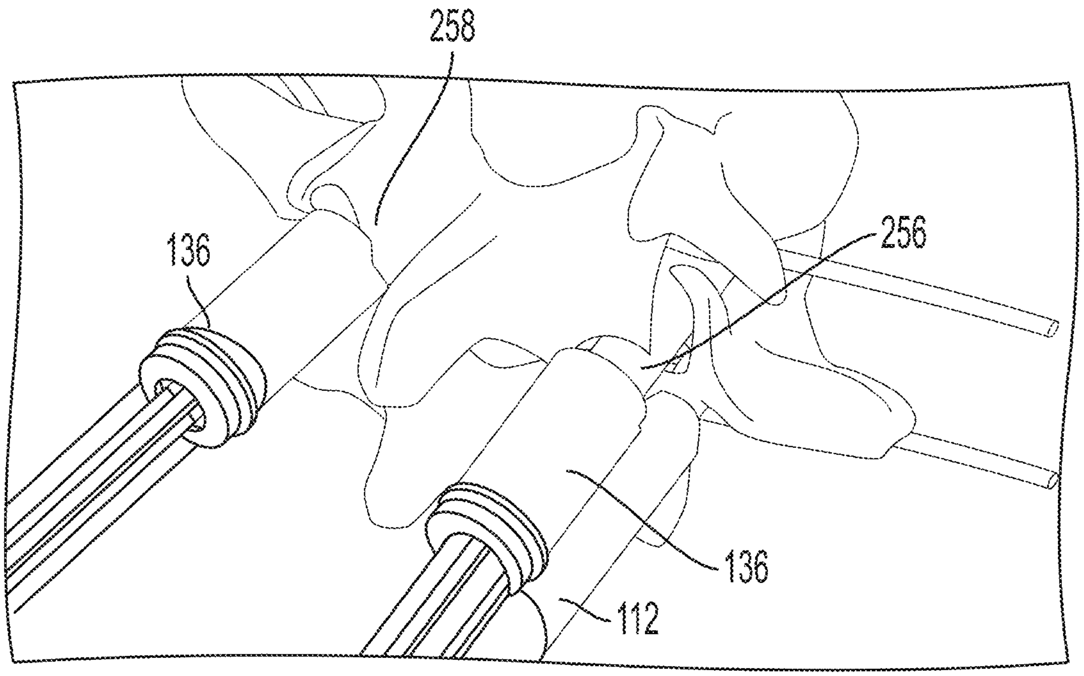
FIG. 9 shows a perspective view of a PePLIF procedure according to certain embodiments of the claimed invention.

FIG. 8 shows a perspective view of this portion of the PePLIF procedure wherein K wires and sequential disc dilators (not shown) are used to safely displace the exiting nerve roots and the dural elements. In some embodiments, the disc dilators are the inner set of dilators and retractor that telescope inside the soft tissue retractor 136. The surgeon inserts a K wire 250 in the right retractor 136 and a K wire 252 in the left retractor 136. Then after one or more K wires 250, 252 have been inserted, sequential disc dilators can be added to displace and protect the nerve roots and dural elements. The K wires are an anchoring instrument for the disc dilators. In some embodiments, the smallest disc dilator may need to displace and protect the exiting nerve root and dural sac initially. Then, the K wires 250, 252 can be introduced into the disc to secure the next disc dilators and the disc retractor. K wires 250, 252 and sequential disc dilators are used because they are flexible, blunt components that will not sever, cut, tear, or harm the nerves. Larger, sequential disc dilators increase the size of the access area to the lateral disc space. FIG. 9 shows a perspective view of this portion of the PePLIF procedure wherein retractors 256, 258 have been applied on top of the disc dilators (not shown) and locked into place. In some embodiments, numerous dilators were applied over the K wires before the disc retractors (inner retractors) were locked in place. Now the area displaced by a right disc retractor 256 and a left disc retractor 258 enable the surgeon to work safely in the lateral disc space without fear of severing, cutting, tearing, or harming the nerve roots, and dural elements. In some embodiments, the final right disc retractor 256 and left disc retractor 258 are angled a few degrees inward and locked onto the soft tissue retractors 136 used for bone removal. In other embodiments, the final right disc retractor 256 and left disc retractor 258 are locked into the pedicle tower 112.

Figure 10:
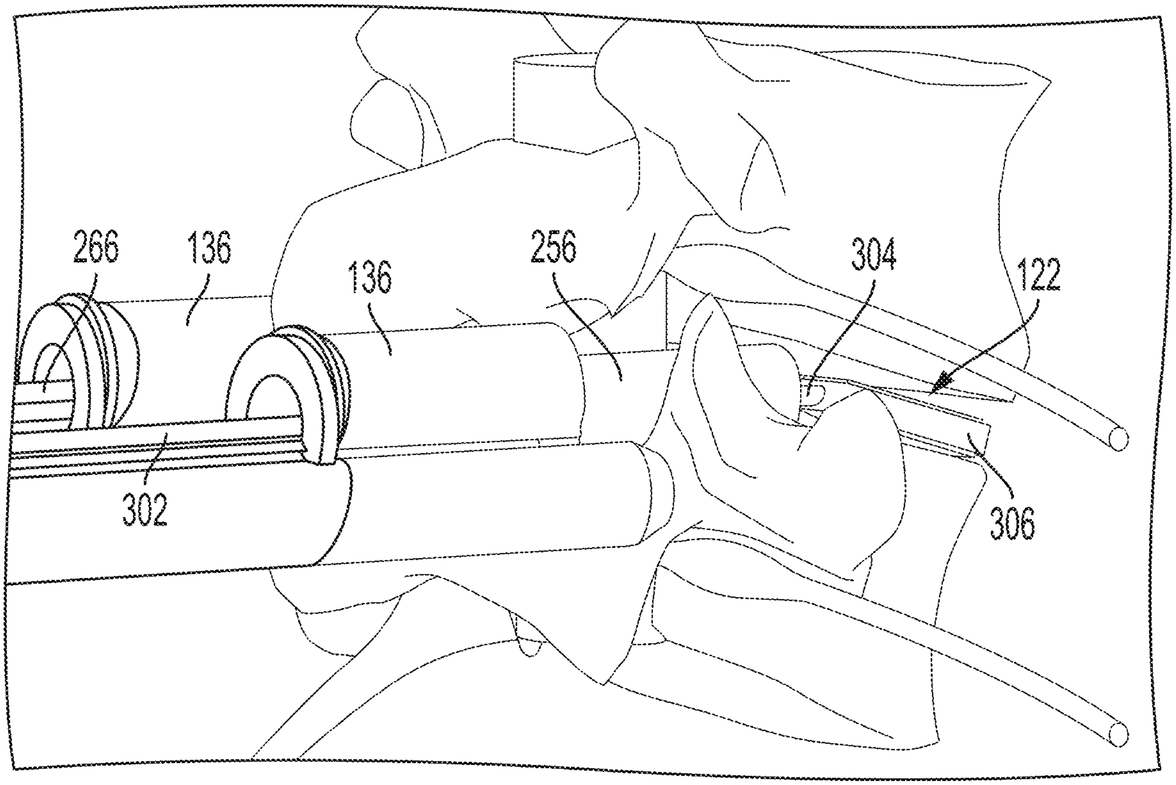
FIG. 10 shows a lateral view of a PePLIF procedure according to certain embodiments of the claimed invention.

FIG. 10 shows a lateral view of this portion of the PePLIF procedure wherein the vertebral disc has been removed. An ultrasonic disc removal and aspiration device (not shown) may be used to remove the vertebral disc by breaking up and aspirating the tissue and cartilage that makes up the disc. The disc removal and aspiration device may be smaller than the bone removal device 210 since it should fit through the cylindrical pathway created by the bone removal device 210. In some embodiments, the tip of the disc removal device may include ultrasonic knives, burs, or an ultrasonic rasp (not shown) to break up the disc tissue and cartilaginous endplate. The disc retractors 256 and 258 protect the exiting nerve roots and the dural elements during this process, so the use of a knife or rasp is possible. The aspiration function of the ultrasonic disc removal and aspiration device removes the broken-up tissue and cartilage from the disc space 122. The ultrasonic disc removal and aspiration device will be further described with reference to FIG. 18. In some embodiments, a portion of the ultrasonic disc removal and aspiration device fits tightly in the disc retractor. Thus, when the surgeon inserts the device into the right position within the retractor, the device takes over and completes the necessary removal of the disc without movement or significant intervention from the surgeon. Thus, the disc removal process becomes more automatic and the surgeon doesn't have to move the device to remove the desired material.

A trial insertion device 302 that will measure the size of the disc space is shown in FIG. 10. The trial insertion device 302 includes an arm 304 to the expandable trial 306. The expandable trial will be discussed in further detail with reference to FIGS. 19A-19C. The trial insertion device must fit through the cylindrical pathway created by the bone removal device and through the soft tissue 136 and disc retractors 256. Unlike the actual implant, the trial insertion device 302 must remain attached to the expandable trial 306 so that it can be inserted and removed during this portion of the procedure. The expandable trial 306 can be expanded to determine the size of the disc space, which informs the surgeon of the necessary size for the implant.

Figure 11:
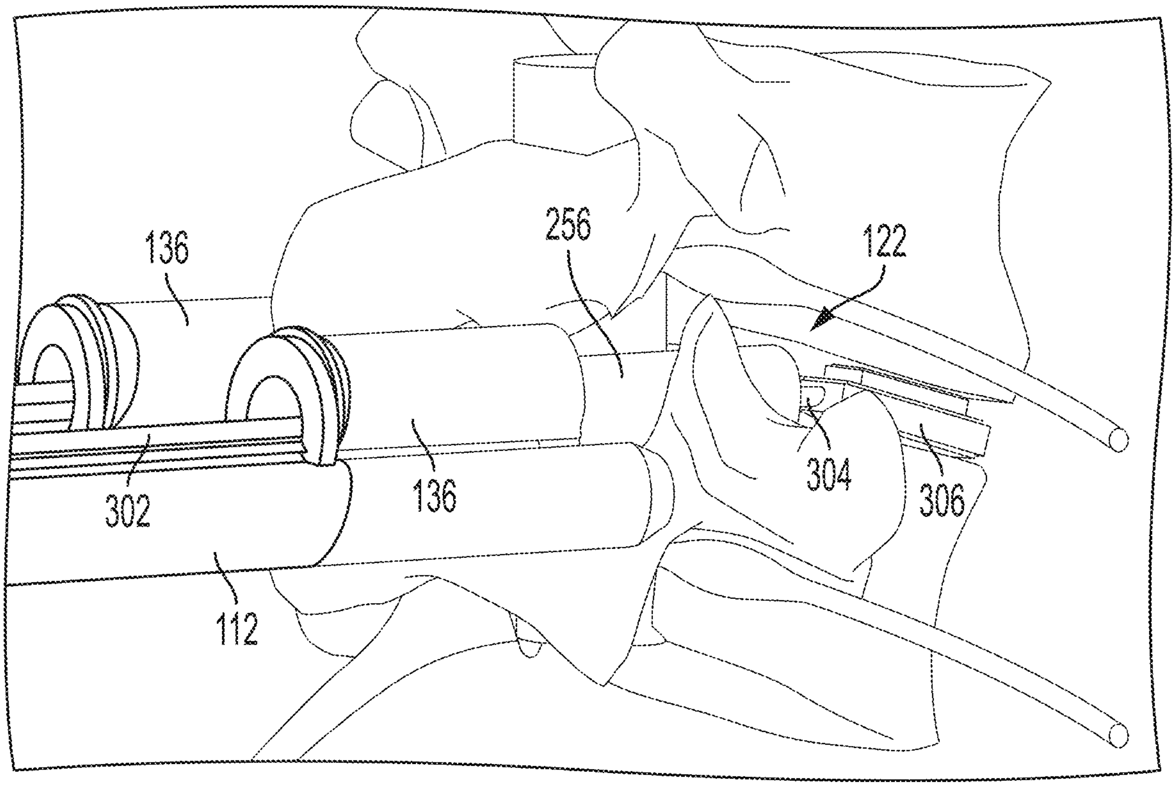
FIG. 11 shows a lateral view of a PePLIF procedure according to certain embodiments of the claimed invention.

FIG. 11 shows a lateral view of this portion of the PePLIF procedure wherein expansion and sizing of the disc space is obtained. More specifically, after the disc is removed the surgeon needs to expand the disc space 122 to (1) obtain an accurate measurement of the area and height of the disc space and (2) insert the implant. In some embodiments, this is done with a trial insertion device 302 that fits inside the retractors 136, 256. The trial insertion device 302 is connected to an expandable disc trial 306 through an arm 304. The expandable disc trial 306 and the arm 304 may also fit through the retractors 136, 256. The arm 304 can be reticulated by the surgeon to apply the expandable disc trial 306 in the proper position. Once inserted, the expandable disc trial 306 can be expanded to the proper size to fill the disc space 122. The surgeon then determines the proper size for the disc implant (not shown) from this expandable disc trial 306, which is important to ensure that the implant is the proper size for the patient. The expandable disc trial 306 must then be compressed again after the measurement so that the surgeon can remove it from the disc space 122. The trial insertion device 302 and the expandable disc trial 306 will be further described with reference to FIG. 19.

Figure 12:
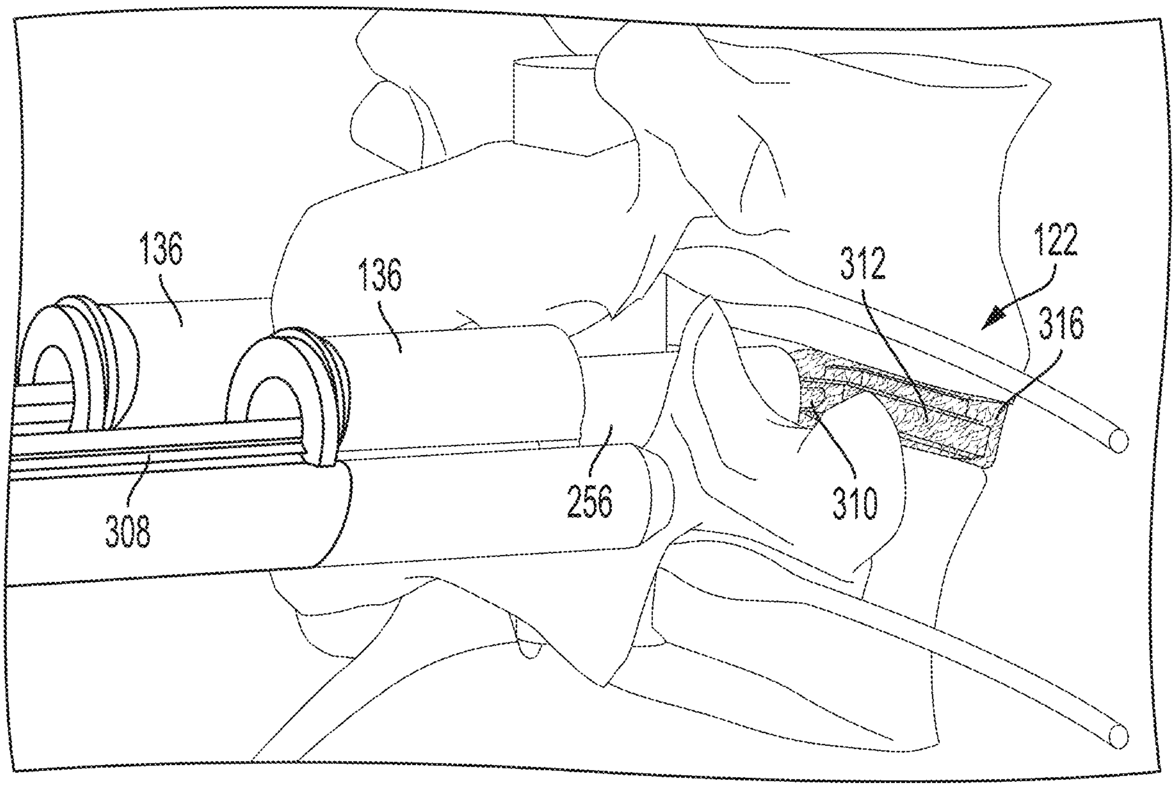
FIG. 12 shows a lateral view of a PePLIF procedure according to certain embodiments of the claimed invention.

FIG. 12 shows a lateral view of this portion of the PePLIF procedure wherein an expandable cage or interbody implant is inserted into the disc space. An interbody implant insertion device 308 may be used to implant an expandable cage 312 into the disc space 122. Similar to the trial insertion device 302, the implant insertion device 308 may fit inside the retractors 136, 256. In some embodiments, the trial insertion device 302 and the implant insertion device 308 may be the same device with different attachments for the expandable disc trial 306 and the expandable cage 312. The implant insertion device 308 may connect to the expandable cage 312 through an arm 310, wherein the expandable cage 312 and the arm 310 may also fit through the retractors 136, 256. The arm 310 can be reticulated by the surgeon to apply the expandable cage 312 in the proper position. In some embodiments, arm 304 and arm 310 may be the same component. While the arm 304 must hold onto the expandable disc trial 306 so that it can be removed from the disc space 122, the arm 310 must be able to detach from the expandable cage 312 so that it can be left in the disc space 122. The implant insertion device 308 must also have the capability to insert bone graft, tissue, and other cellular material 316 into the expandable cage 312, which will assist with fusion, growth, and recovery within the disc space 122. The expandable cage 312 essentially acts as a support and container for this bone graft 316. This additional material (bone graft) allows for bone fusion across the disc space. The implant insertion device 308 and the expandable cage will be further described with reference to FIG. 20.

Figure 13:
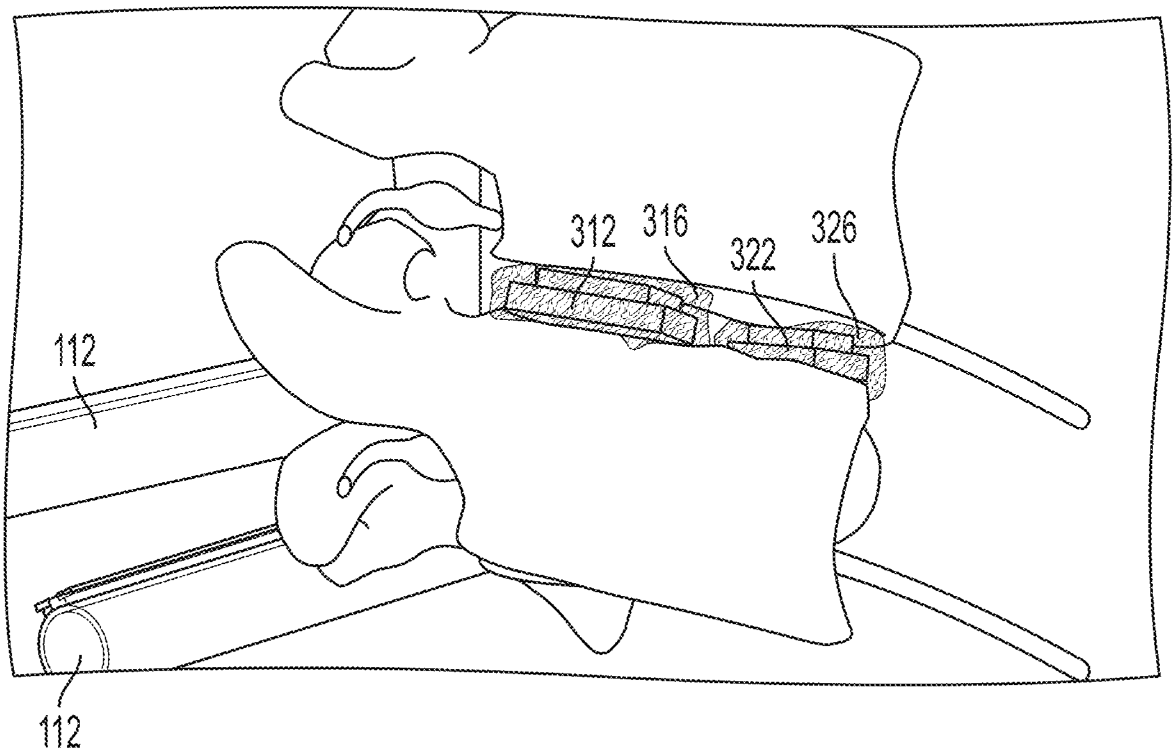
FIG. 13 shows an anterior view of a PePLIF procedure according to certain embodiments of the claimed invention.

FIG. 13 shows an anterior view of this portion of the PePLIF procedure wherein the implant insertion device 308 and the retractors 136, 256 are removed. After the expandable cage 312 has been expanded to the desired volume and filled with bone graft 316, the instruments are removed from the area. FIG. 13 shows that more than one expandable cage 312 may be applied to the disc space 122 in some embodiments. A second expandable cage 322 that is filled with bone graft, tissue, and other cellular material 326 is shown. Both cages 312 (right), 322 (left) may be located laterally against the stronger apophyseal rim of the vertebral endplates. Two expandable cages 312, 322 may provide more support for the patient than a single expandable cage. After both cages 312, 322 are inserted, filled, and detached, the implant insertion device 308 is removed. This is followed by the removal of retractor 256 (not shown), which can be done by unlocking it from retractor 136 (not shown) and sliding it out of the surgical area. Then retractor 136 may be removed by unlocking it from pedicle screw tower 112 and sliding it out of the surgical area. The pedicle screw towers 112 and the pedicle screws (not shown) remain in the patient.

Figure 14:
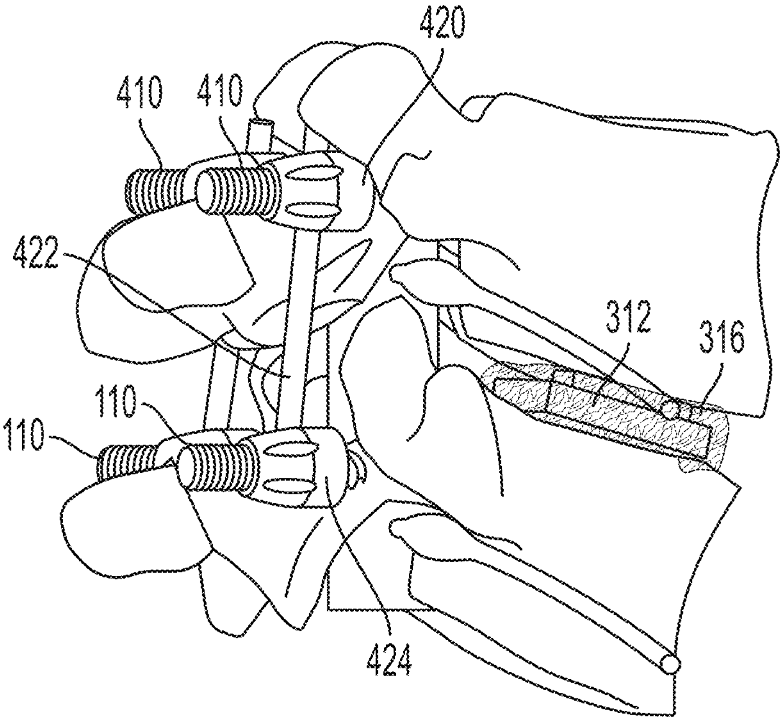
FIG. 14 shows a perspective view of a PePLIF procedure according to certain embodiments of the claimed invention.

FIG. 14 shows a perspective view of a result from the PePLIF procedure where expandable cages have been inserted and the vertebrae have been fused. The right expandable cage 312 and the left expandable cage 322 replace the natural disc that was removed from the patient. This provides vertebral support for the affected area. The original pedicle screws 110 remain in the inferior pedicles. Superior pedicle screws 110 have been inserted in the superior pedicles. Then the right and left rods 422 are inserted percutaneously through the pedicle screw towers 112 (not shown). These rods 422 are tightly secured to the pedicle screw head 420, 424 with set screws 410. The pedicle screw towers 112 have been removed, but the rods 422, pedicle screw heads 420, 424, and set screws 410 provide additional vertebral support for the patient. As described with reference to FIG. 15, the pedicle screw tower enables the surgeon to efficiently apply the rods 422 and the set screws 410 with minimal posterior access to the patient. The pedicle screws 110, 410 expand anterior to the pedicles of the patient.

As shown in FIGS. 1-14, the surgeon may perform the entire surgery percutaneously without the use of a microscope, endoscope, or magnifying loupes. The dilators, retractors, ultrasonic bone and disc removal devices, pedicle screw towers, and other devices disclosed herein enable the surgeon to operate on the desired area through the access areas created by the soft tissue retractors and the disc retractors. While indirect visual assistance may be required through C-arm fluoroscopy or a navigation system (X-ray, CT, or MRI based), this percutaneous access through the posterior of the patient is missing from other procedures. Further, percutaneous surgery has shown to be less disruptive to the patient and leads to a better recovery for the patient.

Figure 15A:
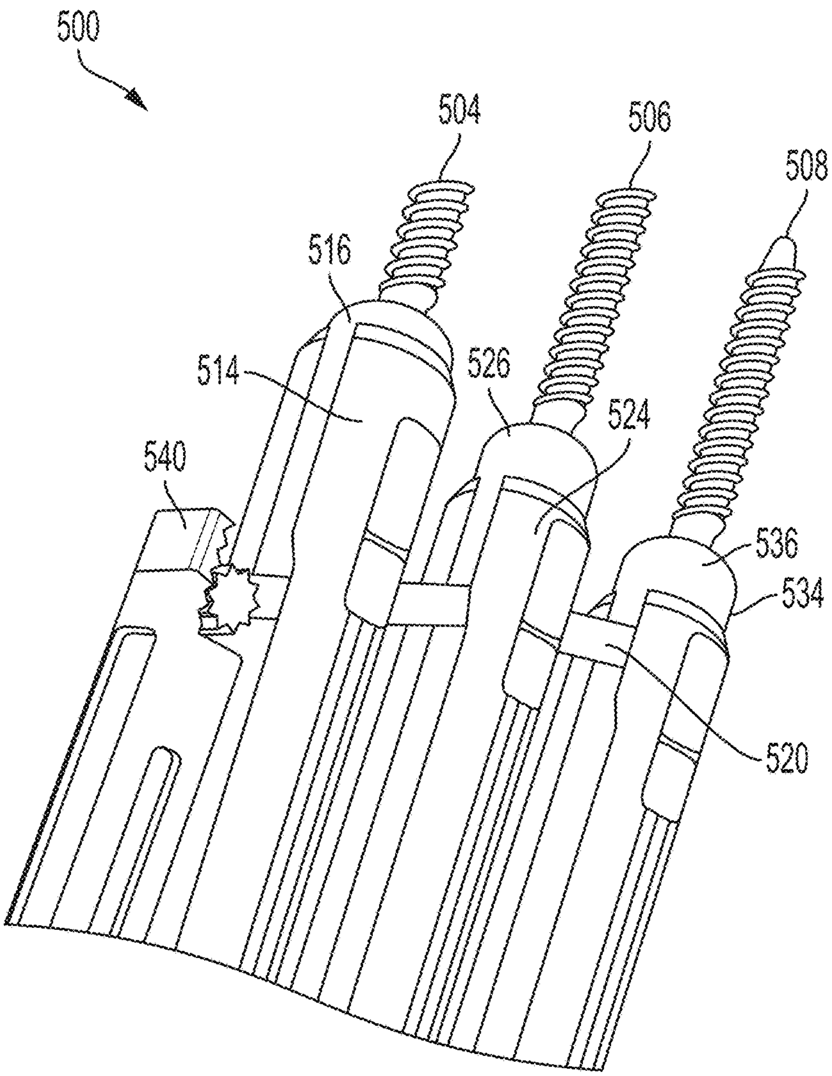
FIG. 15A shows three pedicle screws still attached to their pedicle screw towers and a rod going through the towers and FIG. 15B shows a pedicle screw, rod, and set screw that may be designed to be used in conjunction with certain embodiments of the claimed invention.

FIG. 15A illustrates a perspective view 500 of three pedicle screw towers 514, 524, 534 according to certain embodiments of the present invention. While the pedicle screw tower 112 of FIGS. 1-14 shows the placement of two pedicle screws on each side of the patient's vertebrae, the three pedicle screw towers 514, 524, 534 of FIG. 15A may place two or three pedicle screws in the patient. For a single segment fusion, only two pedicle towers are required, while three pedicle towers may be required for a two-level fusion. The three pedicle screw towers 514, 524, 534 are attached to corresponding screw heads 516, 526, 536 of three corresponding pedicle screws 504, 506, 508. A rod holder 540 and a connection rod 520 going through the pedicle screw towers 514, 524, 534 are also shown. The first pedicle screw tower 514, a second pedicle screw tower 524, and a third pedicle screw tower 534 house a first pedicle screw (thread) 504, a second pedicle screw (thread) 506, and a third pedicle screw (thread) 508, accordingly. The pedicle screw towers 514, 524, and 534 also house a first screw head 516, a second screw head 526, and a third screw head 536. In some embodiments, the screw heads 516, 526, 536 are integral with the pedicle screws 504, 506, 508. A connection rod 520 can be attached to the screw heads 516, 526, 536 through the use of a rod holder 540. The connection rod 520 can be inserted into the shaft of the rod holder 540 and then passed through the screw heads 516, 526, 536 with the rolling head of the rod holder 540. The connection rod 520 is pushed through the screw heads 516, 526, 536 and provides support for the pedicle screws (threads) 504, 506, 508. After the rod 520 makes it into all three screw heads 516, 526, 536 the pedicle screws (threads) 504, 506, 508 can be anchored in place with locking set screws. The connection rod 520 may be anchored into place later in the surgery in case the tower 112 or the retractors need to be adjusted.

Once the trajectory to the disc space is defined, the pedicle screw tower-screw head (carrying the soft tissue dilator/retractor) will need to be locked to the pedicle screw. In order to do this, a very short rod like part/component and set screw may be introduced temporarily (this part may not connect the two pedicle screw heads). Once the interbody fusion has been done, this short rod-like component and set screw may be removed prior to introducing the larger rod with set screws, which does connect two or more pedicle screw heads.

Figure 15B:
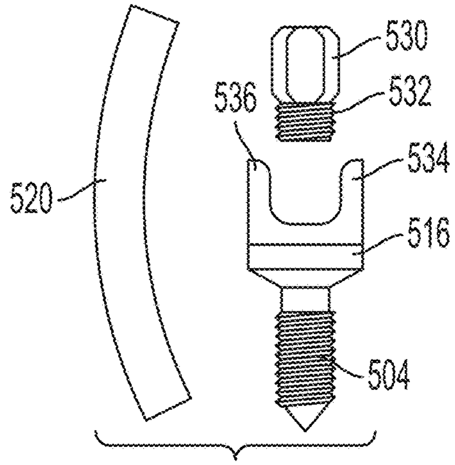

FIG. 15B shows a single pedicle screw (thread) 504 next to the connection rod 520. The pedicle screw head 516 sits on top of the thread 504. The pedicle screw head 516 is a U-shape to account for insertion of the connection rod 520. A right finger 534 and a left finger 536 allow the connection rod to fit inside the pedicle screw head 516. A set screw 530 then can be screwed into the screw head 516 with threads 532. Insertion of this set screw 530 will anchor the connection rod 520 to the pedicle screw 504, and after insertion of all three threaded pins (not shown), the connection rod will anchor all three pedicle screws 504, 506, 508 in the patient. The pedicle screw towers 514, 524, 534 enable the surgeon to insert and screw in all three set screws (i.e., a screwdriver). Then after all three pedicle screws 504, 506, 508 are anchored to the connection rod 520, the pedicle screw towers 514, 524, 534 can be removed. The pedicle screw towers 514, 524, 534 and the rod holder 540 provide a minimal profile that enable the surgeon to work with minimal incisions and agitation to the patient. However, as will be discussed with FIG. 16, the pedicle towers 514, 524, 534 may also be used to insert the dilators and retractors discussed above.

FIG. 16 shows multiple views of a soft tissue (first set) dilator and retractor system 600 that may be used in conjunction with the present invention. The pedicle screw towers 514, 524, 534 mentioned above could represent the pedicle tower 602 in FIG. 16. In some embodiments though, the pedicle tower 602 may be a separate component from the pedicle screw towers 514, 524, 534 that are used to insert the pedicle screws 504, 506, 508 and the connection rod 520. If the pedicle tower 602 represents a single column 514 in FIG. 15A, FIG. 16 presents a cross-section view of the pedicle tower 602. The pedicle tower 602 includes a first rail 622 and a second rail 620. Initially, a first soft tissue dilator 604 is inserted in the pedicle tower 602. The first soft tissue dilator 604 has a first finger 630 and a second finger 632. In conjunction with the shaft on the first soft tissue dilator 604, the first and second fingers 630, 632 allow the surgeon to slide the first dilator 604 into position. As the soft tissue dilator 604 is slid into position it will move any soft tissue out of the way. Then a second soft tissue dilator 606 may be slid into place on top of the first soft tissue dilator 604. This creates more space for the surgeon to use and moves additional soft tissue out of the way. Then a third soft tissue dilator 608 may be slid into place on top of the second soft tissue dilator 606 to create more space for the surgeon.

Once the third soft tissue dilator 608 is in place, a soft tissue retractor 610 may be slid into place over the third soft tissue dilator 608. The soft tissue retractor 610 may include a first finger 642 and a second finger 640 that slide into the first rail 622 and the second rail 620. These connections between the rails 620, 622 and the fingers 640, 642 confirm that the retractor 610 is locked into place with respect to the pedicle tower 602. Accordingly, the connection between the soft tissue retractor 610 and the pedicle tower 602 can be configured or adjusted to ensure proper positioning for the surgeon. And after the soft tissue retractor 610 is locked into place, the first soft tissue dilator 604, second soft tissue dilator 606, and third soft tissue dilator 608 can be removed to leave the space within the soft tissue retractor 610 for the surgeon to work with. A teeth and ridge system could be used to lock the retractor 610 in place. Further, any soft tissue has been moved out of the way by the dilators and retractors leaving the surgeon a safe area to work in. Another advantage to the soft tissue retractor 610 is that now the surgeon can access the desired area through the space within the soft tissue retractor 610.

In some embodiments, this retractor system 600 may be used multiple times. First, the soft tissue retractor system 600 may be used to access the facet joints and lamina for removal of the necessary bone. Then once the bone is removed, the disc retractor system (not shown) may be used to access the disc space. In some embodiments, the soft tissue retractor system 600 is the outer, larger retractor system and the disc retractor system is the smaller, longer set. The disc retractors may telescope through the soft tissue retractor system by locking into the positions that the soft tissue dilators originally occupied (i.e., after the soft tissue dilators are removed, the disc dilators and retractor may be inserted in the same manner). The disc retractors may extend further into the patient than the soft tissue retractors. Thus, the outer soft tissue retractor remains while the smaller disc dilators and retractors are inserted inside this outer retractor for this portion of the surgery. And during the second process, the nerves roots and dural elements are moved out of the way and the surgeon has a great access to the necessary area of the patient. In place of dilators, K wires could be used initially to create space for the disc dilators and retractor. In FIGS. 9-12, reference numeral 136 may be reference numeral 600 in FIG. 16. The disc retractor may flexibly connect to the pedicle tower 602 or the soft tissue retractor 610.

An advantage of the retractor system 600 is that it is adjustable for all patient sizes. A tall patient may need a larger retractor space, while a shorter patient may not. Additionally, different patients may have different shapes and contours of the spine which could lead to different angles required to access the disc space and different sized disc spaces. To adjust for the different patient and disc space sizes, there are different options. First, the first soft tissue dilator blade or stem (the part that connects the pedicle tower 602 to the fingers 630, 632) can be longer or taller. Second, on a larger disc space or patient, there could be 1 or 2 additional soft tissue dilators and 1 or 2 larger soft tissue retractors. Third, the dilator/retractor systems could be longer, which may be important for large or obese patients.

The area of the retractor space may also be adjusted by using different size dilators and/or retractors. The surgeon must determine what space is required for the surgery and adjust the retractor system 600 accordingly. An adjustment of the angle of the retractor system 600 can be made by twisting or turning the pedicle tower 602. For example, a slight move counterclockwise could move the pedicle tower 602 and the retractor 610 to the left. The pedicle tower 602 may include a lock system that enables the surgeon to lock the retractor 610 into the proper position or at the proper angle for the surgery. Typically, the way to lock the pedicle tower 602 and the pedicle screw head (not shown) to the pedicle screw (not shown) is to use a small screw device similar to the set screw. This small device may be similar to the device discussed above in FIG. 15B (short rod-like part or component and set screw). This device gets removed prior to insertion of the rod which allows the pedicle tower 602 and pedicle screw head combination to move again to accommodate the rod. The pedicle screws and heads are polyaxial (meaning the heads of the screws move in any and all directions). The soft tissue dilators and retractors are fixed and move in unison to the pedicle screw tower 602 and pedicle screw head combination.

Figure 17A:
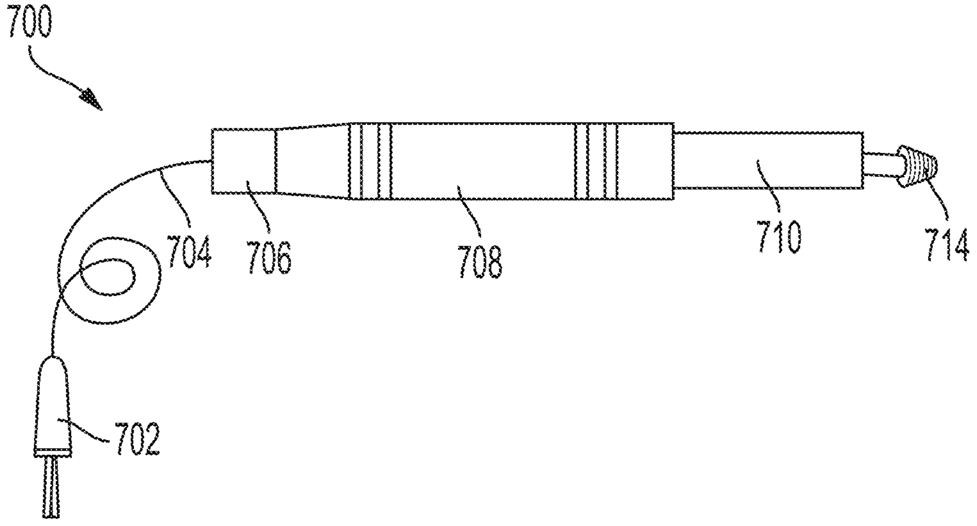
FIGS. 17A, 17B, and 17C show an ultrasonic bone or disc removal and aspiration device that may be designed to be used in conjunction with certain embodiments of the claimed invention.

FIG. 17A shows an ultrasonic bone removal and aspiration device 700 that may be used in certain embodiments of the present invention. This device may also be used to remove the interbody disc or other tissue. The device 700 has a power cord 704 and a plug 702 for connecting to a power supply. A shaft 706 of the device may be controlled by the surgeon and moved accordingly. A grip section 708 may be applied to provide a better grip for the surgeon while he or she operates. The larger size of this shaft 706 and 708 and grip indicate that it may be located outside of the retractor area during the surgery. However, a tube 710 should have a tight fit with the soft tissue retractor (not shown) for access to the facet and lamina or disc space. While the tube 710 of the ultrasonic bone removal device 700 should fit tight inside the soft tissue retractor, the tube of the ultrasonic disc removal device (reference numeral 800 in FIG. 18A) should fit tight inside the disc retractor (not shown). The tube 710 may have a hollow interior for aspirating the bone or tissue as it is broken up during the surgery. This tube 710 may also comprise one or more irrigation channels for assisting with the aspiration of the bone or tissue. Accordingly, the ultrasonic bone removal and aspiration device 700 may include a connection to a water source for supplying the necessary water for the irrigation channels. The tube 710 houses the ultrasonic knife, bur, saw, or rasp 714 and provides a hollow interior for aspirating the bone or tissue as it is broken up during surgery. The ultrasonic movement breaks up the desired area (bone or tissue). As the ultrasonic knife, bur, saw, or rasp 714 circulates, slashes, or circulates in a semi-circle (oscillating ½, ¼, ⅛, 1/16, 1/32, 1/64, etc. of a turn clockwise and counterclockwise), the bone or tissue is broken up and aspirated through the tube 710. Tips for the knives, burs, saws, and rasps are further shown with reference to FIG. 21. All this can be done in the retractor space to avoid encountering any soft tissues during the surgery. In a preferred embodiment, the ultrasonic bone removal and aspiration device 700 comprises a shorter tube 710 that fits tightly in the retractors (soft tissue) without much room for movement. This way the surgeon can insert the device 700 in the retractor and let the device 700 remove all the necessary material without the risk of harming or injuring the patient. With a tight fit, this process may become automatic for the surgeon after the device is inserted properly. In contrast, a longer tube may be used for the disc removal device so that it fits tightly in the disc retractor without much room for movement.

Figure 17B:
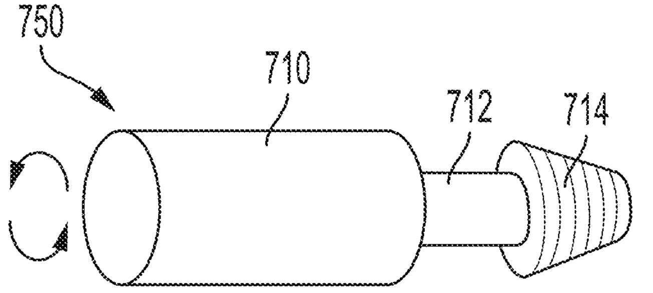
Figure 17C:
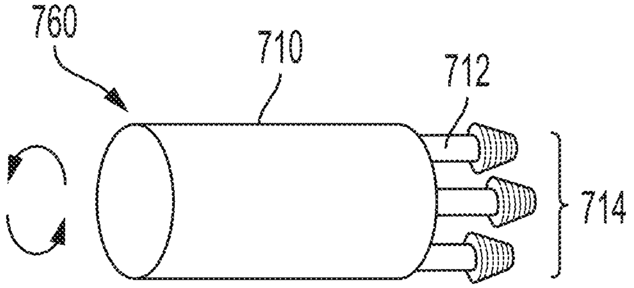

FIGS. 17B and 17C illustrate two cylindrical tips 714 that could be used in certain embodiments of the present invention. FIG. 17B 750 illustrates a single bur tip 714 and tube 710 with connection 712 that can move ultrasonically to break up bone and tissue. FIG. 17C 760 illustrates three bur tips and a tube 710 with connections 712 that may move in a semi-circular rotation or oscillation. A single tip or multiple tips may be used with the ultrasonic bone removal and aspiration device 700. In some embodiments, knife edges, burs, saws, or rasps may be used to break up the bone or tissue and create the corresponding hole or tunnel. This tube 710 may also comprise one or more irrigation channels for assisting with the aspiration of the bone or tissue. As discussed above, the tube 710 is hollow in the center to aspirate the broken-up bone and tissue. Thus, a suction pressure must be applied in the device to remove the bone and tissue. The knife, bur, saw, or rasp 714 can move in a circular movement or other type of movement to create the circular cut. The cylindrical tubes 710 ensure that the device stays in the retractor area and does not harm any structures in the patient.

Ultrasonic bone removal devices provide an advantage over prior drill devices. Ultrasonic devices can be adjustable to the type of material that is being broken up (bone, tissue, disc) and may be gentle for corresponding areas of the patient. The frequency of the device may also be adjusted for the type of material that is being broken up.

Figure 18A:
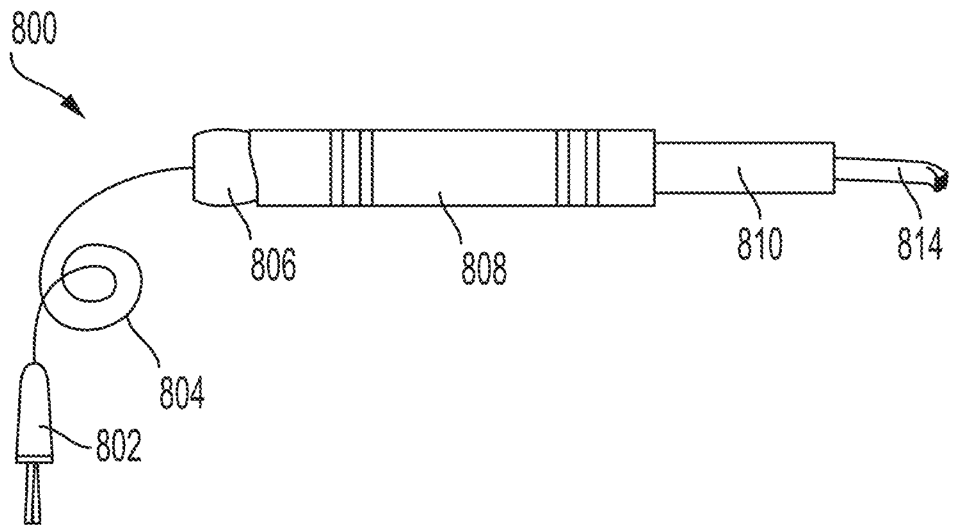
FIGS. 18A, 18B, 18C show an ultrasonic bone or disc removal rasp and aspiration device that may be designed to be used in conjunction with certain embodiments of the claimed invention.

FIG. 18A shows an ultrasonic disc removal rasp and aspiration device 800 that may be used in certain embodiments of the present invention. Burs and saws may also be used in some embodiments of the present invention. This device may also be used to remove the interbody disc or other tissue. The device 800 has a power cord 804 and a plug 802 for connecting to a power supply. A shaft 806 of the device may be controlled by the surgeon and moved accordingly. A grip section 808 may be applied to provide a better grip for the surgeon while he or she operates. The larger size of this shaft 806 and 808 and grip indicate that it may be located outside of the retractor area during the surgery. However, a tube 810 should have a tight fit with the disc retractor and fit inside the disc (inner) retractor area for access to the disc space. The tube 810 may have a hollow interior for aspirating the bone or tissue as it is broken up during the surgery. This tube 810 may also comprise one or more irrigation channels for assisting with the aspiration of the bone or tissue. Accordingly, the ultrasonic disc removal rasp and aspiration device 800 may include a connection to a water source for supplying the necessary water for the irrigation channels. The tube 810 houses the ultrasonic knife, bur, saw, or rasp 814 and provides a hollow interior for aspirating the disc material as it is broken up during surgery. The ultrasonic movement breaks up the desired area (disc or tissue). As the ultrasonic knife, bur, saw, or rasp 814 circulates, oscillates, or slashes, the bone or tissue is broken up and aspirated through the tube 810. Tips for the knives, burs, saws, and rasps are further shown with reference to FIG. 21. All this can be done in the retractor space to avoid encountering any nerves or blood vessels during the surgery. In a preferred embodiment, the ultrasonic disc removal and aspiration device 800 comprises a longer tube 810 that fits tightly in the disc retractors without much room for movement. This way the surgeon can insert the device 800 in the retractor and let the device 800 remove all the necessary material without the risk of harming or injuring the patient. With a tight fit, the process may become more automatic for the surgeon after the device is inserted properly. In contrast, a shorter tube may be used for the bone removal device so that it fits tightly in the soft tissue retractor without much room for movement.

Figure 18B:
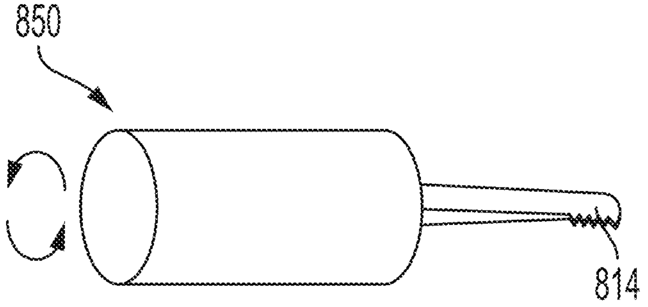
Figure 18C:
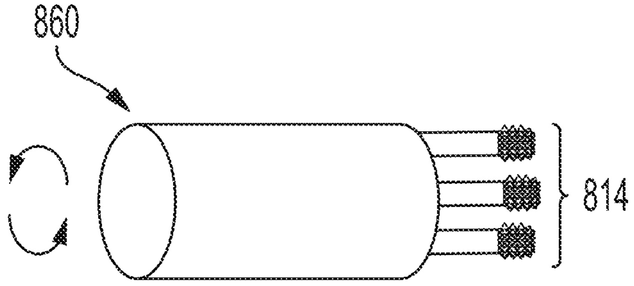

FIGS. 18B and 18C illustrate two cylindrical rasps 850, 860 that could be used in certain embodiments of the present invention. Cylindrical tip 850 contains a rasp 814 with many teeth for breaking up tissue. The rasp 814 is connected to a shaft that ultrasonically moves the tip. Cylindrical tip 860 contains three rasp heads 814 for breaking up bone or tissue. The rasp is connected to a tube 810 that ultrasonically moves the rasps. This movement can be up and down, side to side, circular, or semi-circular (oscillating ½, ¼, or ⅛ of a turn clockwise and counterclockwise). Cylindrical tubes 810 ensure that the device stays in the retractor area and does not harm any structures in the patient.

FIG. 10 shows a lateral view of this portion of the PePLIF procedure wherein the vertebral disc has been removed. An ultrasonic disc removal and aspiration device (not shown) may be used to remove the vertebral disc by breaking up and aspirating the tissue and cartilage that makes up the disc. The disc removal and aspiration device may be smaller than the bone removal device 210 since it should fit through the cylindrical pathway created by the bone removal device 210. In some embodiments, the tip of the disc removal device may include ultrasonic This type of ultrasonic disc removal rasp, bur, or saw provides an advantage over prior rasp devices. The rasp can be adjustable to the type of material that is being broken up (disc, bone, tissue) and may be gentle for corresponding areas of the patient. The frequency of the device may also be adjusted for the type of material that is being broken up.

Figure 19A:
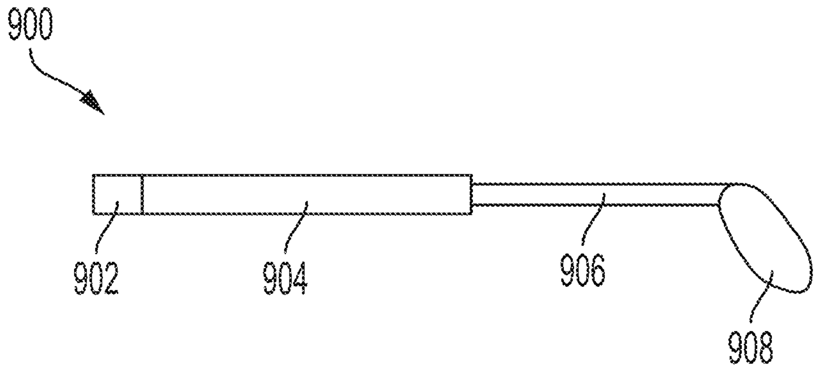
FIGS. 19A, 19B, and 19C show a trial insertion device and expandable disc trial that may be designed to be used in conjunction with certain embodiments of the claimed invention.
Figure 19B:
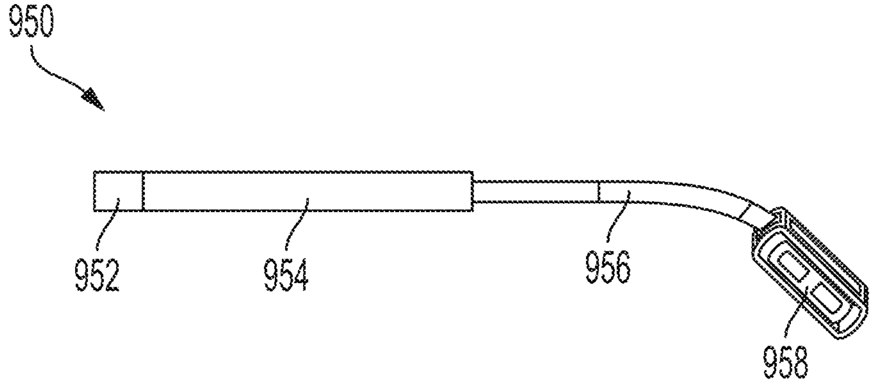
Figure 19C:
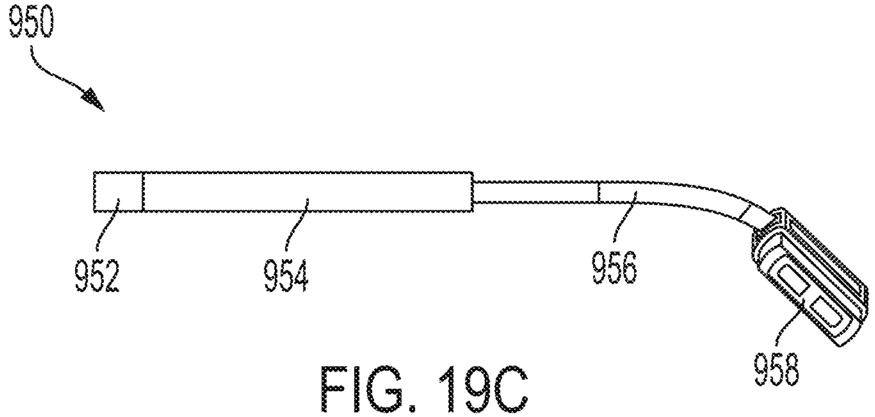

FIGS. 19A, 19B, and 19C illustrate an expandable disc trial device that may be used in certain embodiments of the present invention. The expandable disc trial device 900 has a shaft 902 and a grip section 904 that may be held by the surgeon and moved accordingly. A tube or bar 906 connects the shaft to the expandable trial 908. The tube may be hollow to provide air or fluid to fill the expandable trial 908 when it is inserted in the disc space. The expandable trial 908 is shown as an oval, but it may be configured in other shapes or designs. Once again, the tube or bar 906 and the expandable trial 908 can fit within the retractor space so that it can be inserted in the proper position and avoid any nerves or blood vessels. After the disc space has been prepared or suctioned, the expandable trial 908 is inserted in the disc space. At this time, air, water, or other material can flow into the expandable trial 908 for expansion. Once the expandable trial 908 is at the prior size, the surgeon may remove the expandable trial 908 to determine the proper size for the implant or cage. In other embodiments, the device may be able to track how much air or water has been pumped into the expandable trial 908 and then determine the proper size for the implant or cage. This information could be provided on a display on the expandable disc trial device 900.

FIGS. 19B and 19C show an alternative embodiment for the expandable trial device 950. The expandable disc trial device 950 has a shaft 952 and a grip section 954 that may be held by the surgeon and moved accordingly. A tube or bar 956 connects the shaft to the expandable trial 958. This expandable trial 958 may be expanded through mechanical means. For example, an endless screw that expands the trial vertically may be used. Similar to a car jack, the trial is the jack that expands as the endless screw is actuated. More specifically, the device 950 may control the expansion of the trial by actuating a lift mechanism for raising or lowering the expandable trial 958. FIG. 19B may illustrate the expandable trial 958 when inserted and FIG. 19C may illustrate the expandable trial 958 after it has been expanded (vertically). The expandable trial 958 is shown as a rectangle in this figure, but it may be configured in other shapes or designs. Once again, the tube or bar 956 and the expandable trial can fit within the retractors space so that it can be inserted in the proper position and avoid any nerves or blood vessels. Once the expandable trial 958 is at the proper size, the surgeon may remove the expandable trial 958 to determine the proper size for the implant or cage. In other embodiments, the device 950 may be able to provide the expanded height or pressure of the expandable trial 958 and then determine the proper size for the implant or cage. This information could be provided on a display on the expandable disc trial device 950.

Figure 20A:
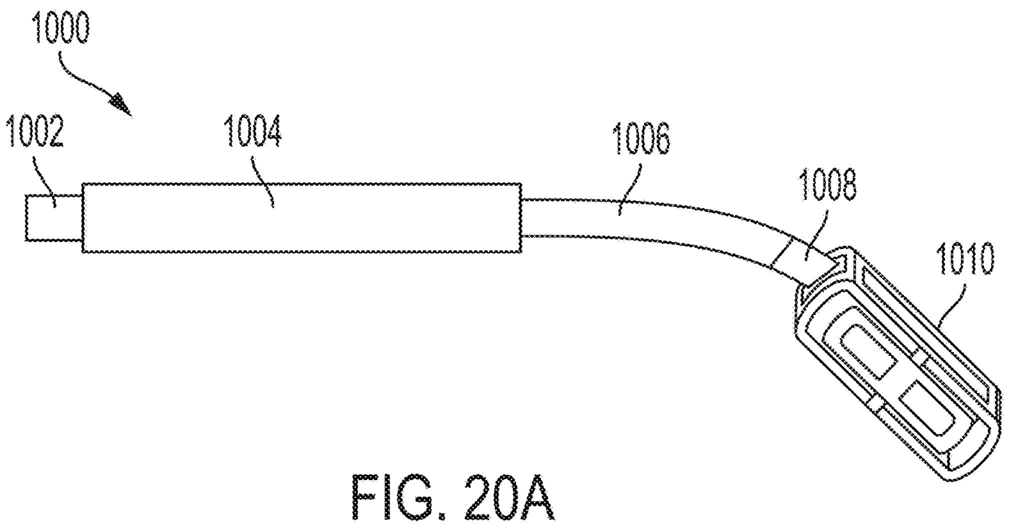
FIGS. 20A, 20B, and 20C show an implant insertion device and expandable cage that may be designed to be used in conjunction with certain embodiments of the claimed invention.
Figure 20B:
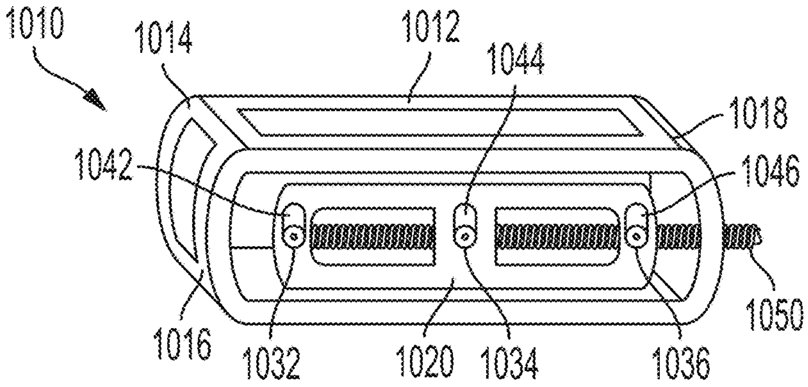
Figure 20C:
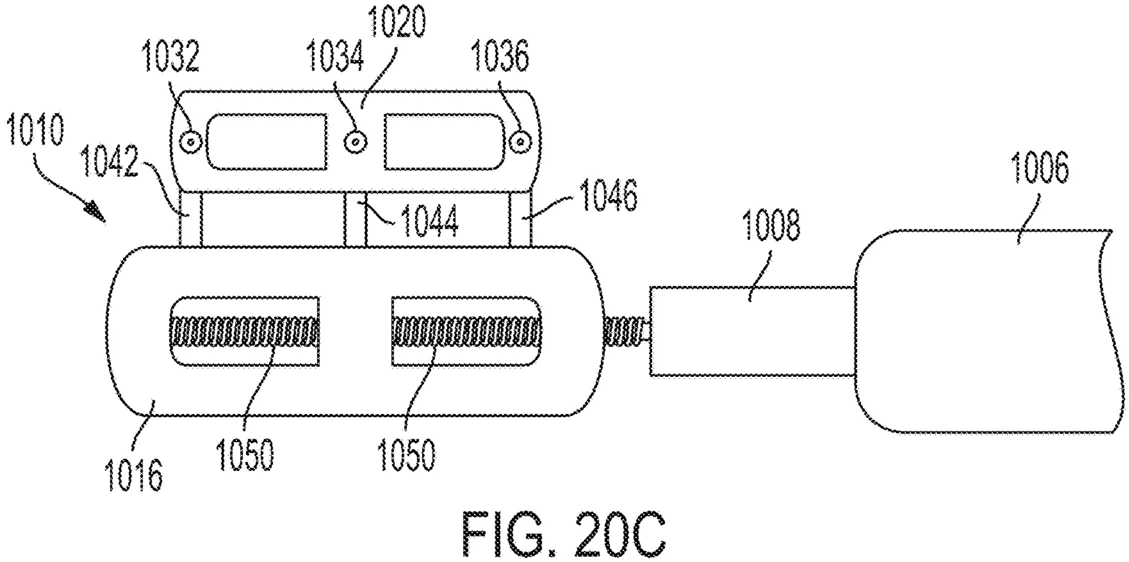

FIGS. 20A, 20B, and 20C illustrate an implant insertion device and expandable cage that may be used in the present invention. Unlike the expandable trial device 900, the implant insertion device 1000 must be able to separate from an expandable cage 1010 to leave the cage 1010 in the disc space. A button or actuator 1002 may be used to detach the expandable cage 1010 when it is in the proper position. This actuator 1002 may be connected to a shaft 1004 which can be adjusted and moved by the surgeon. A tube 1006 is connected to the shaft 1004. The tube 1006 may have a smaller diameter so that it can be inserted into the retractor space. A connector 1008 may provide the connection between the tube 1006 and the expandable cage 1010. This connector 1008 must be able to grasp an expandable cage

1010, but also detach from the expandable cage 1010. Many different mechanisms could be used for this connector 1008, including a clasp mechanism, screw mechanism, finger mechanism, rail mechanism, and many others. The actuator 1002 may be directly or indirectly connected to the connector 1008 to control the attachment and the detachment of the expandable cage 1010. The implant insertion device 1000 should be hollow or contain a reservoir inside of the shaft so that bone material (graft) can flow into the expandable cage 1010 when it is expanded. If hollow, a port on the device near the button 1002 or shaft 1004 could provide access to the bone material that would then pass through the tube 1006 and the connector 1008 to fill up the expanded cage 1010. If a reservoir is used, then the bone material should be pumped into the shaft 1004 before the surgical procedure. Then the implant insertion device 1000 can be activated to release the bone material into the expandable cage 1010 by the surgeon. Once again, the bone material would pass through the tube 1006 and the connector 1008 to fill up the expanded cage 1010. The addition of this bone graft assists with bone growth, healing, and support within the disc space.

FIGS. 20B and 20C further illustrate one embodiment of an expandable cage 1010 that may be used with the present invention. In this embodiment, a screw mechanism may be used to expand the cage 1010. Three pins or complementary screws 1042, 1044, 1046 can be connected to a screw 1050. The three pins or complementary screws 1042, 1044, 1046 are then connected to an upper plate 1020 of the expandable cage 1010. The upper plate 1020 may be connected to the three pins or complementary screws 1042, 1044, 1046 through three corresponding fasteners 1032, 1034, 1036. Through this mechanism the upper plate 1020 may extend or contract based upon the movement of the screw 1050. Circular movement of the screw one way extends the upper plate 1020, while circular movement in the opposite way contracts the upper plate 1020. The expandable cage 1010 has a first side plate 1016, a second side plate 1014, a third side plate 1018, and a lower plate 1012. When placed in the disc space, the lower plate 1012 may be placed at the bottom of the disc space, while the upper plate 1020 can raise to expand the cage 1010. Much of the cage 1010 is hollow and the plates 1012, 1014, 1016, 1018 may have numerous holes or voids for the influx of bone material after insertion. After the cage 1010 has been expanded to the proper size by the surgeon, the bone material can be pumped in such that it overflows and pours out of the expandable cage. One screw, two screws, or three screws could be used in certain embodiments of the present invention. Further, the expandable cage 1010 could operate similar to a car jack with an endless screw. As the screw is actuated, the x-shaped jack may expand the cage 1010.

FIG. 20C illustrates the attachment and detachment of the implant insertion device 1000 and the expandable cage 1010. As discussed above, the connector 1008 may be connected to the tube 1006. The connector 1008 may be attached to the expandable cage 1010 during insertion. After the cage 1010 has been inserted and expanded and the bone material has been deposited in the expandable cage 1010, the implant insertion device 1000 must detach from the expandable cage 1010. In this embodiment, a latch mechanism or finger mechanism may detach the connector from the screw 1050 so that the implant insertion device 1000 may be removed through the retractor space. In other embodiments, the screw 1050 may detach from the three pins 1042, 1044, 1046 so that the screw 1050 and the connected implant insertion device 1000 can be removed from the retractor space. As mentioned above, many different expandable cage mechanisms are within the scope of the present invention. For example, instead of a screw mechanism an x-shaped jack mechanism or lift mechanism could be used. The CONCORDE LIFT expandable interbody device by DePuy Synthes provides one example for a jack mechanism that may be used in certain embodiments of the present invention. The ELITE expandable interbody fusion system by Spineology, Inc. provides another example for a jack mechanism that may be used in certain embodiments of the present invention. An air pump mechanism could also be used to expand the cage 1010. Further, many different detachment mechanisms are also within the scope of the present invention.

Figure 21:
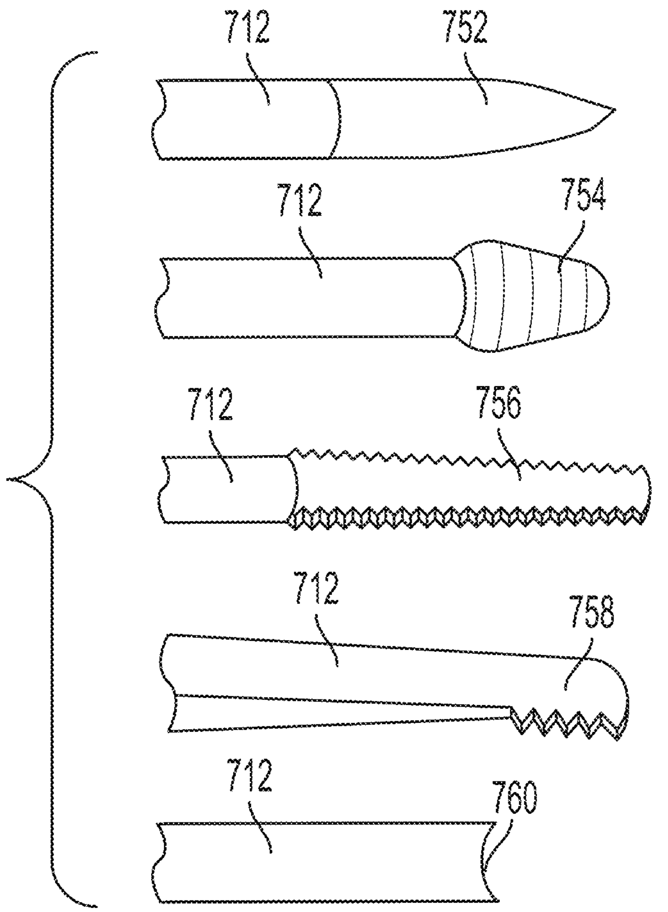
FIG. 21 shows various tips for the ultrasonic bone or disc removal devices that may be designed to be used in conjunction with certain embodiments of the claimed invention.

FIG. 21 illustrates various tips for the bone or disc removal devices disclosed in FIG. 17A, 17B, 17C, 18A, 18B, or 18C. One or more of these tips may be used to remove bone or tissue in the present invention. Depending upon the patient and the type of PeLIF procedure, a surgeon may choose to use one or more blades, burs, saws, rasps, or sharpened circular tips in the PeLIF procedure. A blade is shown in the top illustration 752. A bur is shown in the second illustration 754. A dual-blade saw is shown in the third illustration 756. A rasp is shown in the fourth illustration 758. A circular saw/blade is shown in the fifth illustration 760. Rasps, side rasps, or single-blade saws (see FIGS. 18A and 18C) may also be used by the surgeon. As disclosed above, numerous configurations for the bone or disc removal devices are within the scope of the present invention.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A medical device for use with a patient comprising:

at least one first retractor that is configured to be connected to a pedicle screw structure; and at least one second retractor that is configured such that at least a portion of said second retractor may be inserted into an interior of said first retractor and is configured to provide access to a disc space of the patient through an interior of said second retractor;

wherein said second retractor is configured to be adjustable within said first retractor to displace tissue of the patient in or adjacent to the disc space.

2. The medical device of claim 1 wherein said at least one first retractor is further configured to be adjusted to enable access to at least a portion of a facet joint of said patient.

3. The medical device of claim 1 wherein said at least one first retractor is further configured to be indirectly connected to said pedicle screw structure.

4. The medical device of claim 1 wherein said at least one second retractor is further configured to be directly connected to said first retractor.

5. The medical device of claim 1 further comprising a first dilator that is configured to be connected to said pedicle screw structure and is configured to be removed from said interior of said first retractor.

6. The medical device of claim 5 wherein said first dilator is further configured to be indirectly connected to said pedicle screw structure.

7. The medical device of claim 1 further comprising a first dilator that is configured to be connected to said at least one first retractor and is configured to be removed from said interior of said second retractor.

8. A retractor system for use during surgery on a patient comprising:

at least one first retractor that is configured to be connected to a screw structure that is configured to be anchored to a bone of said patient;

at least one second retractor that is configured to be inserted in an interior space of said first retractor and is configured to provide access to a space inside of the bone of said patient; and wherein said second retractor is configured to be adjustable within said interior space of said first retractor to displace tissue of the patient in or adjacent to said space inside of the bone of said patient.

9. The retractor system of claim 8 wherein said at least one first retractor is further configured to be adjusted to enable access at least a portion of said bone of said patient through the interior of said first retractor.

10. The retractor system of claim 8 wherein said at least one first retractor is further configured to be indirectly connected to said screw structure.

11. The retractor system of claim 8 further comprising a first dilator that is configured to be connected to said screw structure and is configured to be removed from said interior of said first retractor.

12. The retractor system of claim 11 wherein said first dilator is further configured to be indirectly connected to said pedicle screw structure.

13. The retractor system of claim 8 wherein said space inside of the bone of said patient is a disc space within a spine of said patient.

14. A medical device for use with a patient comprising:

at least one first retractor that is configured to be anchored to a spine of a patient;

at least one second retractor that is configured to be inserted into an interior of said first retractor and is configured to provide access to a disc space of the patient through an interior of said second retractor; and wherein said second retractor is configured to be adjustable to displace tissue of the patient in or adjacent to the spine.

15. The medical device of claim 14 wherein said first retractor is configured to be connected to a pedicle of said patient.

16. The medical device of claim 15 wherein said second retractor is configured to be connected to said first retractor, wherein said second retractor is adjustable with respect to said first retractor.

17. The medical device of claim 14 wherein said second retractor is further configured to be adjustable to displace tissue of the patient in or adjacent to said disc space.

18. The medical device of claim 14 wherein said first retractor is further configured to provide access to a facet joint of said patient through said interior of said first retractor.

19. The medical device of claim 14 further comprising a first dilator that is configured to be adjustable within said interior of said first retractor and is configured to be removed from said interior of said first retractor.

20. The medical device of claim 19 wherein said first dilator is configured to be adjustable to displace tissue of the patient in or adjacent to said disc space.

* * * * *